(12) United States Patent
Wang et al.

(10) Patent No.: US 9,284,601 B2
(45) Date of Patent: Mar. 15, 2016

(54) MICROFLUIDIC SYSTEM FOR HIGH-THROUGHPUT, DROPLET-BASED SINGLE MOLECULE ANALYSIS WITH LOW REAGENT CONSUMPTION

(71) Applicant: The Johns Hopkins University, Baltimore, MD (US)

(72) Inventors: Tza-Huei Wang, Baltimore, MD (US); Kelvin J. Liu, Baltimore, MD (US); Christopher M. Puleo, Glenville, NY (US); Tushar D. Rane, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/136,671

(22) Filed: Dec. 20, 2013

(65) Prior Publication Data
US 2014/0106462 A1 Apr. 17, 2014

Related U.S. Application Data

(62) Division of application No. 13/147,742, filed as application No. PCT/US2010/025933 on Mar. 2, 2010, now Pat. No. 8,637,301.

(60) Provisional application No. 61/156,637, filed on Mar. 2, 2009.

(51) Int. Cl.
| | |
|---|---|
| *C12Q 1/68* | (2006.01) |
| *C12M 1/00* | (2006.01) |
| *C12M 1/36* | (2006.01) |
| *C12M 1/34* | (2006.01) |
| *C12M 3/00* | (2006.01) |
| *G01N 15/06* | (2006.01) |
| *G01N 21/64* | (2006.01) |
| *B01L 3/00* | (2006.01) |
| *G01N 1/38* | (2006.01) |
| *G01N 15/14* | (2006.01) |
| *B01L 7/00* | (2006.01) |
| *G01N 1/40* | (2006.01) |
| *G01N 15/00* | (2006.01) |

(52) U.S. Cl.
CPC ......... *C12Q 1/6825* (2013.01); *B01L 3/502753* (2013.01); *B01L 3/502769* (2013.01); *G01N 1/38* (2013.01); *G01N 15/1484* (2013.01); *G01N 21/6458* (2013.01); *B01L 7/52* (2013.01); *B01L 2200/0678* (2013.01); *B01L 2200/10* (2013.01); *B01L 2300/088* (2013.01); *B01L 2400/0481* (2013.01); *B01L 2400/0655* (2013.01); *G01N 2001/4027* (2013.01); *G01N 2015/0038* (2013.01); *G01N 2015/1493* (2013.01); *G01N 2021/6419* (2013.01); *G01N 2021/6421* (2013.01); *Y10T 436/143333* (2015.01)

(58) Field of Classification Search
USPC .............. 435/6.1, 283.1, 286.5, 286.7, 287.1, 435/288.5; 422/68.1, 82.08
See application file for complete search history.

(56) References Cited

U.S. PATENT DOCUMENTS

| 6,614,030 B2 | 9/2003 | Maher et al. |
| 7,315,376 B2 | 1/2008 | Bickmore, Jr. et al. |
| 2004/0175298 A1 | 9/2004 | Choikhet |
| 2006/0257893 A1 | 11/2006 | Takahashi et al. |
| 2008/0014576 A1 | 1/2008 | Jovanovich et al. |
| 2010/0118300 A1 | 5/2010 | Wang et al. |

OTHER PUBLICATIONS

Agrawal et al., "Real-time detection of virus particles and viral protein expression with two-color nanoparticle probes". *J. Virol.* Jul. 2005, vol. 79, No. 13: pp. 8625-8628.
Camacho et al., "Direct quantification of mRNA expression levels using single molecule detection". *J. Biotechnol*, 2004, 107:107-114.
Castro et al., "Single-Molecule Detection of Specific Nucleic Acid Sequences in Unamplified Genomic DNA", *Anal. Chem.*, 1997, 69, 3915-3920.
Chao et al., "Quantification of Low Concentrations of DNA Using Single Molecule Detection and Velocity Measurement in a Microchannel", *Fluoresc.*, 2007, 17, 767-774.
Chou et al., "A microfabricated device for sizing and sorting DNA molecules". *Proceedings of the National Academy of Sciences*, Jan. 1999, vol. 96: pp. 11-13.
Chou et al., "A Microfabricated Rotary Pump", *Biomed. Microdevices*, 2001, 3, 323-330.
Craighead, "Future lab-on-a-chip technologies for interrogating individual molecules", *Nature* 2006, 442:387-393.
Crevillen et al., "Real sample analysis on *microfluidic* devices", *Talanta*, 2007, 74, 342-357 (DOI:10.1016/j.talanta.2007.10.019).
D'Antoni et al., "Rapid quantitative analysis suing a single molecule counting approach", *Anal. Biochem.*, 2006, 352, 97-109 (DOI:10.1016/j.ab.2006.01.031).
De Mello et al., "Hydrodynamic focusing in microstructures: Improved detection efficiencies in subfemtoliter probe volumes". *J AppL Phys.* 2007, 101:084903-1-084903-8.
De Mello, "Seeing single molecules", *Lab. Chip*, 2003, 3, 29N-34N (DOI:10.1039/b304585b [doi]).
Dorre et al., "Highly efficient single molecule detection in microstructures". *J. Biotechnol.* 2001, 86:225-236.
Enderlein et al., "Molecular Shot Noise, Burst Size Distribution, and Single-Molecule Detection in Fluid Flow: effects of Multiple Occupancy", *J. Phys. Chem. A*, 1998, 102, 6089-6089-6094.
Filippova et al., "Quantifying double-strand breaks and clustered damages in DNA by single-molecule laser fluorescence sizing". *Biophys. J.* 2003, 84:1281-1290.

(Continued)

*Primary Examiner* — Narayan Bhat
(74) *Attorney, Agent, or Firm* — Venable LLP; Henry J. Daley

(57) ABSTRACT

A microfluidic device for a confocal fluorescence detection system has an input channel defined by a body of the microfluidic device, a sample concentration section defined by the body of the microfluidic device and in fluid connection with the input channel, a mixing section defined by the body of the microfluidic device and in fluid connection with the concentration section, and a detection region that is at least partially transparent to illumination light of the confocal fluorescence detection system and at least partially transparent to fluorescent light when emitted from a sample under observation as the sample flows through the detection region.

9 Claims, 10 Drawing Sheets

(56) References Cited

OTHER PUBLICATIONS

Foquet et al., "DNA fragment sizing by single molecule detection in submicrometer-sized closed fluidic channels". *Anal. Chem.* 2002, 74:1415-1422.

Gao et al., "Silicon Nanowire Arrays for Label-Free Detection on DNA", *Anal. Chem.*, 2007, 79, 3291-3297.

Goodwin et al., "Rapid sizing of individual fluorescently stained DNA fragments by flow cytometry". *NucL Acids Res.* 1993 21:803-806.

Ha et al., "Initiation and re-initiation of DNA unwinding by the *Escherichia coli* Rep helicase". *Nature* 2002,419:638-641.

Haab et al., "Single-molecule detection of DNA separations in microfabricated capillary electrophoresis chips employing focused molecular streams". *Anal. Chem.* 1999, 71:5137-5145.

Habbersett et al., "An analytical system based on a compact flow cytometer for DNA fragment sizing and single-molecule detection". *Cytometry A* 2004, 60:125-134.

Haeberle et al., "Microfluidic platforms for lab-on-a-chip applications", *Lab. Chip*, 2007, 7, 1094-1110 (DOI:10.1039/b706364b).

Heo et al., "Characterization and Resolution of Evaporation-Mediated Osmolality Shifts That Constrain Microfluidic Cell Culture in Poly(dimethylsiloxane) Devices", *Anal. Chem.*, 2007, 79, 1126-1134 (DOI:10.1021/ac061990v).

Huang et al., "Counting low-copy number proteins in a single cell". *Science* 2007, 315:81-84.

Huisken, et al., "Optical Sectioning Deep Inside Live Embryos by Selective Plane Illumination Microscopy". *Science* 2004, 305:1007-1009.

International Search Report for PCT/US2010/025933 dated Oct. 28, 2010.

Knemeyer et al., "Probes for Detection of Specific DNA Sequences at the Single-Molecule Level", *Anal. Chem.*, 2000, 72, 3717-3724.

Kuswandi, et al., Optical sensing system for microfluidic devices: A review, Analytica Chimica Acta., Oct. 10, 2007, vol. 601., Issue 2, pp. 141-155.

Leng et al., "Microevaporators for Kinetic Exploration of Phase Diagrams", *Phys. Rev. Lett.*, 2006, 96, 084503-1-084503-4.

Leng et al., "Microfluidic Exploration of the HPase Diagram of a Surfactant/Water Binary System", *Langmuir*, 2007, 23, 2315-2317.

Li et al., "Molecule by Molecule Direct and Quantitative Counting on Antibody-Protein Complexes in Solution", *Anal. Chem.*, 2004, 76, 4446-4451 (DOI:10.1021/ac049512c).

Li et al., "Ultrasensitive coincidence fluorescence detection of single DNA molecules". *Anal. Chem.* 2003, 75:1664-1670.

Lipman, et al., "Single-molecule measurement of protein folding kinetics". *Science* 2003, 301:1233-1235.

Liu et al, Quantitative Confocal Spectroscopy—Rectifying the Limitations of Single Molecule Detection, 2008, Proceedings of the 3rd IEEE Int. Conf. on Nano/Micro Engineered and Molecular Systems, pp. 1189-1192.

Liu et al., "Cylindrical illumination Confocal Spectroscopy: Rectifying the Limitations on Confocal Single Molecule Spectroscopy through One-Dimensional Beam Shaping", *Biophys. Journal*, 95(6), 2964-2975, Sep. 2008.

Lyon et al., "Confinement and Detection of Single Molecules in Submicrometer Channels". *Anal. Chem.* 1997, 69:3400-3405.

Marme et al., "Sensitive bioanalysis-combining single-molecule spectroscopy with mono-labeled self-quenching probes", *Anal. Bioanal Chem.*, 2007, 388, 1075-1085 (DOI:10.1007/s00216-007-1365-1).

Melin et al., "Microfluidic Large-Scale Integration: The Evolution of Design Rules for Biological Automation". *Annu. Rev. Biophys. Biomol. Struct.*, 2007, 36, 213-231 (DOI:10.1146/annurev.biophys.36.040306.132646).

Moore, "Purification and concentration of DNA from aqueous solutions." Curr Protoc Immunol. 2001, pp. 10.1.

Nair et al., "Performance limits of nanobiosensors", *Appl. Phys. Lett.*, 2006, 88, 233120.

Neely et al., "A isngle-molecule method for the quantitation of microRNA gene expression", *Nat. Methods*, 2006, 3, 41-46 (DOI:10.1038/nmeth825).

Nolan et al., "A Simply Quenching Method for Fluorescence Background Reduction and Its Application to the Direct, Quantitative Detection of Specific mRNA", *Anal. Chem.*, 2003, 75, 6236-6243.

Patolsky et al., "Nanowire sensors for medicine and the life sciences", *Nanomed.*, 2006, 1, 51-65.

Pons et al., "Solution-phase single quantum dot fluorescence resonance energy transfer". *J. Am. Chem. Soc.* 2006, 128:15324-15331.

Puleo et al., "Coupling confocal fluorescence detection and recirculating microfluidic control for single particle analysis in discrete nanoliter volumes", *Lab Chip*, 2008, 8, 822-825 (DOI:10.1039/b717941c).

Puleo et al., "Coupling Evaporation-Based Microfluidic Concentration and Confocal Fluorescence Spectroscopy", Micro Electro Mechanical Systems, 2008. MEMS 2008. IEEE 21st International Conference on, 2008, 200-203.

Ralf et al., "High-speed confocal fluorescence imaging with a novel line scanning microscope". *J. Biomed. Opt.* 2006, 11:064011-1-064011-14.

Randall et al., "Permeation-driven flow in poly9dimethylsiloxane) microfluidic devices", *Proc. Natl. Acad. Sci. U S. A.*, 2005, 102, 10813-10818 (DOI:10.1073/pnas.0503287102).

Roulet, et al., Performance of an Integrated Microoptical System for Fluorescence Detection in Microfluidic Systems, Anal. Chem., 2002, vol. 74, No. 14. pp. 3400-3407.

Schrum et al., "Microchip flow cytometry using electrokinetic focusing". *Anal. Chem.* 1999, 71:4173-4177.

Second Generation Evaporation/Concentration System for Life Science Laboratories,2008 [online], [retrieved May 24, 2012], Retrieved from Genevac, Ltd., EZ-Bio : www.genevac.com<http://www.genevac.com>, 2pp.

Serra et al, Microfluidic-Assisted Synthesis of Polymer Particles, 2008, Chem. Eng. Technol. 31, 1099-1115.

Sharma et al, Development of an evaporation-based microfluidic sample concentrator, 2008, Proc. of SPIE, 6886 pp. 1-9.

Sharma et al, Development of an evaporation-based microfluidic sample concentrator, 2008, Proc. of SPIE, 6886, Date support document, pp. 1 and 2.

Sheehan et al., "Detection Limits for Nanoscale Biosensors", *Nano Lett.*, 2005, 5, 803-807 (DOI:10.1021/n1050298x WWI).

Tang et al., "Real-time monitoring of nucleic acid ligation in homogenous solutions using molecular beacons", *Nucleic Acids Res.*, 2003, 31, e148.

Teh et al., "Droplet microfluidics", *Lab. Chip*, 2008, 8, 198-220 (DOI:10.1039/13715524g).

Tsourkas et al., "Hybridization kinetics and thermodynamics of molecular beacons", *Nucleic Acids Res*, 31, 1319-1330.

Unger et al., "Monolithic Microfabricated Valves and Pumps by Multilayer Soft Lithography", *Science*, 2000, 288, 113-116 (DOI:8400 [pii].

Van Orden et al., "High-throughput flow cytometric DNA fragment sizing". *Anal. Chem.* 2000, 72:37-41.

Wabuyele et al., "Approaching real-time molecular diagnostics: single-pair fluorescence resonance energy transfer (spFRET) detection for the analysis of low abundant point mutations in K-ras oncogenes". *J. Am. Chem. Soc.* 2003, 125:6937-6945.

Walker et al., "An evaporation-based microfluidic sample concentration method", *Lab. Chip*, 2002, 2, 57-61 (DOI:10.1039/b202473j [doi]).

Wang et al., "Single-molecule tracing on a fluidic microchip for quantitative detection of low-abundance nucleic acids". *J. Am. Chem. Soc.* 2005, 127:5354-5359.

Werner et al., "Increasing the resolution of single pair fluorescence resonance energy transfer measurements in solution via molecular cytometry". *Anal. Chem.* 2007, 79:3509-3513.

Xi et al., "Evaluation of Microfuidic Biosensor Development Using Microscopic Analysis of Molecular Beacon Hybridization Kinetics", *Biomed. Microdev.*, 2005, 7, 7-12.

Yao, Bo, et al., A microfluidic device based on gravity and electric force driving for flow cytometry and fluorescence activated cell sorting, LabChip, Nov. 10, 2004, vol. 4, pp. 603-607.

(56) References Cited

OTHER PUBLICATIONS

Yeh et al., "Homogeneous point mutation detection by quantum dot-mediated two-color fluorescence coincidence analysis", *Nucleic Acids Res.*, 2006, 34, e35 (D01:34/5/e35 [pii]; 10.1093/nar/gkl021 [doi]).

Yeh et al., "Quantum dot-mediatied biosendsing assays for specific mucleic acid detection", *Nanomedicine*, 2005, 1, 115-121 (DOI:10.1016/j.nano.2005.03.004.

Yeh et al., "Single-Molecule Detection and Probe Strategies for Rapid and Ultrasensitive Genomic Detection", *Curr. Pharm. Biotechnol.*, 2005, 6, 453-461.

Yeh et al., "Tunable Blinking Kinetics of Cy5 for Precise DNA Quantification and Single-Nucleotide Difference Detection", *Biophys.* Jul. 1, 2008, 95, 729-737 (DOI:10.1529/biophysj.107.127530).

Zhang et al., "Comparative quantification of nucleic acids using single-molecule detection and molecular beacons". *The Analyst* 2005, 130:483-488.

Zhang et al., "Single-quantum-dot-based DNA nanosensor", *Nat. Mater.*, 2005, 4, 826-831.

Zimmermann et al., "Continuous flow in open microfluidics using controlled evaporation", *Lab. Chip*, 2005, 5, 13551359 (DOI:10.1039/b510044e).

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catccgctgc ctcccgtagg agtg                                           24
```

MICROFLUIDIC SYSTEM FOR HIGH-THROUGHPUT, DROPLET-BASED SINGLE MOLECULE ANALYSIS WITH LOW REAGENT CONSUMPTION

CROSS-REFERENCE TO RELATED APPLICATIONS

This application is a Divisional of U.S. application Ser. No. 13/147,742, filed Aug. 3, 2011, which is a National Stage of U.S. national stage application under 35 U.S.C. 371 of PCT/US2010/025933, filed Mar. 2, 2010, which claims priority to U.S. Provisional Application No. 61/156,637, filed Mar. 2, 2009, the contents of which are incorporated herein by reference.

This invention was made using U.S. Government support under NSF Grant No. BES-0546012 and NIH Grant No. CA120742. The U.S. Government has certain rights in this invention.

SEQUENCE LISTING

The instant application contains a Sequence Listing which has been submitted in ASCII format via EFS-Web and is hereby incorporated by reference in its entirety. Said ASCII copy, created on Aug. 7, 2013, is named 02240-305944_SL.txt and is 702 bytes in size.

BACKGROUND

1. Field of Invention

The current invention relates to microfluidic systems, and more particularly to microfluidic systems for high-throughput, droplet-based single molecule analysis with low reagent consumption.

2. Discussion of Related Art

Single molecule optical techniques have existed for decades and have provided researchers with techniques that enable dynamic measurements on the single-molecule scale that are not accessible in bulk. However, these same techniques have not translated well into the genomic era, where variations of molecular amplification techniques, such as polymerase chain reaction (PCR), remain the basis for detecting the accumulation of genetic alterations in cells and tissues. Several technical challenges remain for single molecule detection (SMD) techniques to gain widespread acceptance in genomic research applications (H. Craighead, *Nature*, 2006, 442, 387-393; A. J. de Mello, *Lab. Chip*, 2003, 3, 29N-34N; L. A. Neely, S. Patel, J. Garver, M. Gallo, M. Hackett, S. McLaughlin, M. Nadel, J. Harris, S. Gullans and J. Rooke, *Nat. Methods*, 2006, 3, 41-46). First, sample throughput for these platforms should approach that of current technologies, such as multiwell PCR or microarrays. This will require extremely efficient transfer of individual molecules to the micron-sized optical probes used in the SMD platforms. Second, assay times for SMD techniques should be minimized. Currently, many single molecule applications run for hours due to the inefficient probe-target interactions that occur when using extremely dilute and unamplified biological samples (L. A. Neely, S. Patel, J. Garver, M. Gallo, M. Hackett, S. McLaughlin, M. Nadel, J. Harris, S. Gullans and J. Rooke, *Nat. Methods*, 2006, 3, 41-46). And last, SMD platforms should adopt complementary technologies (C. M. Puleo, H. C. Yeh, K. J. Liu and T. H. Wang, *Lab Chip*, 2008, 8, 822-822-825; S. Y. Teh, R. Lin, L. H. Hung, and A. P. Lee. Lab. Chip, 2008, 8(2), 198-220) that are amenable to automation and universal implementation, thus lifting the current limitations due to highly technical setup and operational procedures involved with single molecule data collection.

Single molecule detection (SMD) allows the study of molecular properties without the bias of ensemble averaging. Although methods using scanning probe, resonant, and electrical sensors are being developed (Craighead, H. 2006, Future lab-on-a-chip technologies for interrogating individual molecules, *Nature* 442:387-393), it can also be performed using confocal spectroscopy, an optical detection method in which a collimated laser beam is focused into a diffraction-limited spot about 1 femtoliter in volume and used to excite single fluorescent molecules. While biomolecules are often tethered to solid substrates for in depth study of molecular dynamics, continuous flow systems can offer higher throughput and other advantages for quantitative applications. An example of SMD is confocal spectroscopy of molecules in free solution under continuous flow. SMD can be ideally suited as a platform for the detection of rare biomolecules such as nucleic acids (Li, H., L. Ying, J. J. Green, S. Balasubramanian, and D. Klenerman. 2003. Ultrasensitive coincidence fluorescence detection of single DNA molecules. *Anal. Chem.* 75:1664-1670; Camacho, A., K. Korn, M. Damond, J. F. Cajot, E. Litborn, B. Liao, P. Thyberg, H. Winter, A. Honegger, P. Gardellin, and R. Rigler. 2004. Direct quantification of mRNA expression levels using single molecule detection. *J. Biotechnol.* 107:107-114; Wabuyele, M. B., H. Farquar, W. Stryjewski, R. P. Hammer, S. A. Soper, Y. W. Cheng, and F. Barany. 2003. Approaching real-time molecular diagnostics: single-pair fluorescence resonance energy transfer (spFRET) detection for the analysis of low abundant point mutations in K-ras oncogenes. *J. Am. Chem. Soc.* 125:6937-6945; Zhang, C. Y., S. Y. Chao, and T. H. Wang. 2005. Comparative quantification of nucleic acids using single-molecule detection and molecular beacons. *The Analyst* 130:483-488), proteins, and small ligands (Pons, T., I. L. Medintz, X. Wang, D. S. English, and H. Mattoussi. 2006. Solution-phase single quantum dot fluorescence resonance energy transfer. *J. Am. Chem. Soc.* 128:15324-15331), the characterization of biomolecular interactions and molecular processes (Lipman, E. A., B. Schuler, O. Bakajin, and W. A. Eaton. 2003. Single-molecule measurement of protein folding kinetics. *Science* 301:1233-1235; Ha, T., I. Rasnik, W. Cheng, H. P. Babcock, G. H. Gauss, T. M. Lohman, and S. Chu. 2002. Initiation and re-initiation of DNA unwinding by the *Escherichia coli* Rep helicase. *Nature* 419:638-641), DNA sizing (Habbersett, R. C., and J. H. Jett. 2004. An analytical system based on a compact flow cytometer for DNA fragment sizing and single-molecule detection. *Cytometry A* 60:125-134), and pathogen detection (Agrawal, A., R. A. Tripp, L. J. Anderson, and S. Nie. 2005. Real-time detection of virus particles and viral protein expression with two-color nanoparticle probes. *J. Virol.* 79:8625-8628).

Although in principle SMD can be highly quantitative, its current implementations limit its accuracy, throughput, and practical applicability. The minute size of the SMD observation volume enables high signal-to-noise ratio detection of even single fluorescent molecules due to highly suppressed background levels. However, the diffraction-limited observation volume that enables SMD also significantly hampers its application in quantification and burst parameter determination. Since the observation volume in standard SMD is typically much smaller than the channel used for molecular transport, a condition of low mass detection efficiency is created where the large majority of molecules escape detection. We define the mass detection efficiency as the total proportion of molecules flowing through the channel that are detected.

These mass detection efficiencies are usually 1% or less (Haab, B. B., and R. A. Mathies. 1999, Single-molecule detection of DNA separations in microfabricated capillary electrophoresis chips employing focused molecular streams. *Anal. Chem.* 71:5137-5145). For example, assuming 1) that all molecules passing within the observation volume are detected, 2) a radially symmetric, ellipsoidal, confocal observation volume with $1/e^2$ radii of 0.5×1 μm, and 3) detection within a 100 μm ID microcapillary, the resultant mass detection efficiency would be less than 0.05%. This necessitates extended data acquisition times and increased sample volumes for the detection of rare molecules (Wang, T. H., Y. H. Peng, C. Y. Zhang, P. K. Wong, and C. M. Ho. 2005, Single-molecule tracing on a fluidic microchip for quantitative detection of low-abundance nucleic acids, *J. Am. Chem. Soc.* 127: 5354-5359). In addition, since the observation volume profile is Gaussian in shape and highly non-uniform, a molecule's specific trajectory through the detection region will have a large influence on the emitted and collected fluorescence bursts, adding significant variability and uncertainty to not only the burst parameters but also their rate of detection.

The majority of approaches to rectify these short-comings have centered on controlling the molecular trajectory using either hydrodynamic (de Mello, A. J., and J. B. Edel. 2007, Hydrodynamic focusing in microstructures: Improved detection efficiencies in subfemtoliter probe volumes. *J. Appl. Phys.* 101:084903; Werner, J. H., E. R. McCarney, R. A. Keller, K. W. Plaxco, and P. M. Goodwin, 2007, Increasing the resolution of single pair fluorescence resonance energy transfer measurements in solution via molecular cytometry. *Anal. Chem.* 79:3509-3513) or electrokinetic (Haab, B. B., and R. A. Mathies., 1999, Single-molecule detection of DNA separations in microfabricated capillary electrophoresis chips employing focused molecular streams. *Anal. Chem.* 71:5137-5145; Wang, T. H., Y. H. Peng, C. Y. Zhang, P. K. Wong, and C. M. Ho. 2005. Single-molecule tracing on a fluidic microchip for quantitative detection of low-abundance nucleic acids. *J. Am. Chem. Soc.* 127:5354-5359; Schrum, D. P., C. T. Culbertson, S. C. Jacobson, and J. M. Ramsey. 1999. Microchip flow cytometry using electrokinetic focusing. *Anal. Chem.* 71:4173-4177) forces as well as nanochannel confinement (Foquet, M., J. Korlach, W. Zipfel, W. W. Webb, and H. G. Craighead. 2002. DNA fragment sizing by single molecule detection in submicrometer-sized closed fluidic channels. *Anal. Chem.* 74:1415-1422; Dorre, K., J. Stephan, M. Lapczyna, M. Stuke, H. Dunkel, and M. Eigen. 2001. Highly efficient single molecule detection in microstructures. *J. Biotechnol.* 86:225-236; Lyon, W. A., and S. Nie. 1997. Confinement and Detection of Single Molecules in Submicrometer Channels. *Anal. Chem.* 69:3400-3405). However, these approaches have limitations in their practical application due to effectiveness, throughput limitations, reagent consumption and ease of use, for example. Therefore, there remains a need for improved single molecule detection systems and methods.

SUMMARY

A microfluidic device for a confocal fluorescence detection system according to an embodiment of the current invention has an input channel defined by a body of the microfluidic device, a sample concentration section defined by the body of the microfluidic device and in fluid connection with the input channel, a mixing section defined by the body of the microfluidic device and in fluid connection with the concentration section, and a detection region that is at least partially transparent to illumination light of the confocal fluorescence detection system and at least partially transparent to fluorescent light when emitted from a sample under observation as the sample flows through the detection region.

A microfluidic detection system according to an embodiment of the current invention has a microfluidic device having a detection region defined by a body of the microfluidic device, an objective lens unit arranged proximate the microfluidic device, an illumination system in optical communication with the objective lens unit to provide light to illuminate a sample through the objective lens unit, and a detection system in optical communication with the objective lens unit to receive at least a portion of light that passes through the objective lens unit from the sample. The microfluidic device has an input channel defined by the body of the microfluidic device, a sample concentration section defined by the body of the microfluidic device and in fluid connection with the input channel, and a mixing section defined by the body of the microfluidic device and in fluid connection with the concentration section. The detection region is at least partially transparent to illumination light from the illumination system and at least partially transparent to fluorescent light when emitted from a sample under observation as the sample flows through the detection region.

A method of detecting particles according to an embodiment of the current invention includes providing a sample comprising particles to be detected and a fluid in which the particles are at least one of suspended or dissolved, concentrating the sample by removing at least a portion of the fluid using a microfluidic device to provide a concentrated sample, mixing the concentrated sample with a reagent to label the particles to be detected using the microfluidic device, and detecting the particles after the mixing based on a response of the labels. The sample is greater than about 1 μl and less than about 1 ml, and the concentrated sample is reduced in volume by a factor of at least 100.

BRIEF DESCRIPTION OF THE DRAWINGS

In FIGS. 2A and 2B the combined microevaporator/rotary SMD microdevice has a control layer (lighter grey) that shows the evaporation membrane, rotary pump, and isolation valves. Target accumulation is accomplished by solvent removal from the fluidic layer (black, inlet labeled i.) through the pervaporation membrane (inlet labeled ii.). Following target accumulation the concentrated sample plug is transferred to the SMD-Rotary Chamber for probe hybridization and detection; probes and hybridization buffer are introduced through separate inlets (labeled iii.). In FIG. 2C the side sectional view of the operating microevaporator, prior to sample transfer into the detection chamber is shown. Solvent removal through the pervaporation membrane is compensated by convection from the sample reservoir, while actuation of the accumulation valve enables target collection at the dead end.

DETAILED DESCRIPTION

Figure 1A:
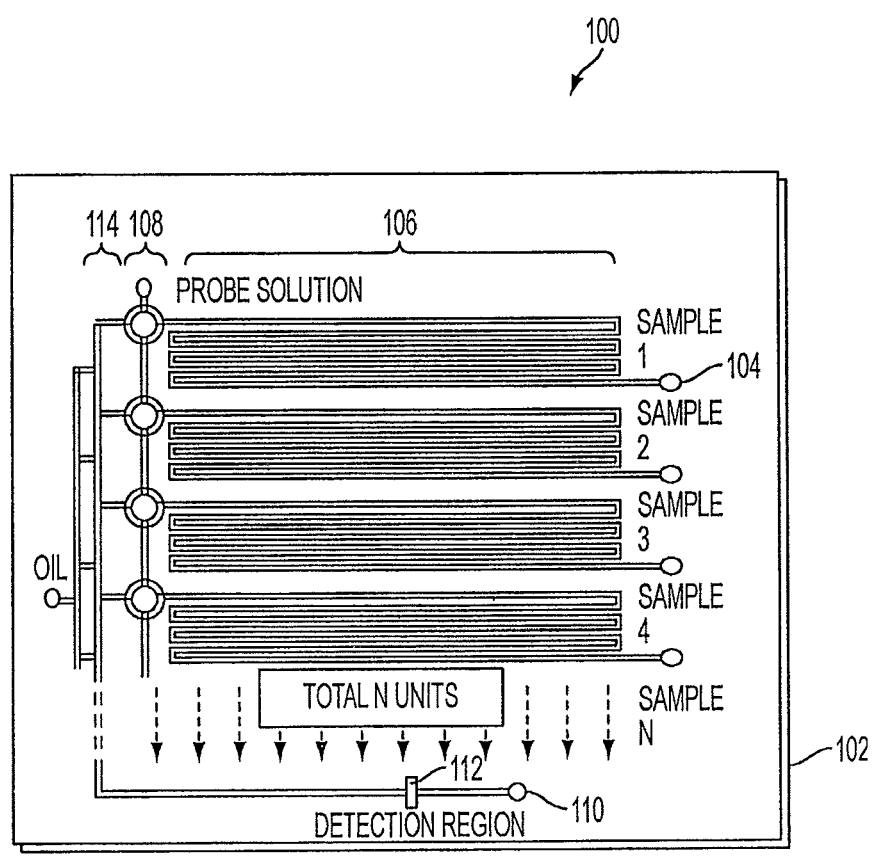
FIG. 1A is a schematic illustration of a microfluidic device according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention.

All references cited herein are incorporated by reference as if each had been individually incorporated.

The terms light, optical, optics, etc are not intended to be limited to only visible light in the broader concepts of the current invention. For example, they could include infrared and/or ultraviolet regions of the electromagnetic spectrum according to some embodiments of the current invention.

An embodiment of the current invention is directed to a microfluidic device that includes inline micro-evaporators to concentrate biological target molecules within nano-to-picoliter-sized water-in-oil droplets. These droplets can serve as both low-volume reactors for parallel sample processing of the concentrated samples, and digital compartments that enable ordered transfer for downstream SMD analysis. Utilization of the evaporators as microliter-to-picoliter interconnects between the macroscopic world and single molecule microanalytical systems can solve problems of conventional devices such as those discussed above that hinder the widespread acceptance and utilization of SMD. First, solvent removal within the evaporators transports and confines the molecular contents of large sample volumes to the downstream droplets, which can be swept through laser-illuminated, confocal fluorescence detection volumes. The intradroplet, molecular detection efficiency at this point can be as high as about 100% using cylindrical illumination confocal spectroscopy (CICS) (K. H. Liu and T. H. Wang. Biophys. Journal, 95(6), 2964-2975, 2008) and pushing the entire droplet through a laser-illuminated sheet; however, the optical probe can be made to match a variety of operational parameters and the platform is not limited to only CICS detection. Unlike traditional continuous flow SMD platforms, sample throughput and the kinetics of probe-target interactions of single molecule assays conducted in accordance with some embodiments of the current invention are limited by the speed of solvent removal, which is a controllable device parameter. Therefore, run times for single molecule assays can be greatly reduced due to target enrichment within the droplets, which facilitates probe-target interactions at relatively high concentrations. At these concentrations, droplet-based microfluidics becomes an advantageous complementary technology to single molecule optical platforms, allowing rapid analysis of molecules trapped within parallel reaction compartments in an automated and controllable fashion. And, in addition to simply making SMD amenable to high-throughput studies of genetic alterations, microfluidic systems and methods according to some embodiments of the current invention can open new biological applications that were previously unachievable. For instance, microfluidic loading and quick analytical schemes according to some aspects of the current invention can make high-speed, fluorescence-activated molecular sorting ("FACS for molecules") a possibility, within controllable reaction compartments that can be manipulated and observed nearly at the will of the genomic researcher.

FIG. 1A is a schematic illustration of a microfluidic device 100 for a confocal fluorescence detection system according to an embodiment of the current invention. The microfluidic device 100 comprises a body 102 that defines an input section 104, a sample concentration section 106 in fluid connection with the input section 104, a mixing section 108 in fluid connection with the concentration section 106, and an output channel 110 in fluid connection with the mixing section 108. The output channel 110 has a detection region 112 that is at least partially transparent to illumination light of the confocal fluorescence detection system and at least partially transparent to fluorescent light when emitted from a sample under observation as the sample flows through the detection region 112.

The body 102 of the microfluidic device 100 can be a composite structure having a plurality of layers and/or components combined according to the particular application. For example, the body 102 defines a fluid channel layer therein which can include a patterned layer attached to a substrate. The body 102 can further include an actuation layer in some embodiments of the current invention. The actuation layer can include structures to provide valves at selected regions of the microfluidic device 100.

The concentration section 106 has a total of N concentration components in parallel in this example. The invention is not limited to a particular number N of concentration components and also includes the case in which N=1 such that there is no parallelism in that particular example. However, parallel structures in which N=2, 3, 4 or a much larger number may be useful for many applications. Each concentration component of the concentration section 106 is in fluid connection with an input channel of the input section 104. This allows selected fluids to be directed into each concentration component of the concentration section 106.

The microfluidic device 100 further comprises a droplet generator 114 defined by the body 102 of the microfluidic device 100. The droplet generator 114 is arranged in fluid connection between the mixing section 108 and the output channel 110. Although not shown in detail in FIG. 1A, the droplet generator 114 can be a hydrodynamic-focusing droplet generator or a pneumatic valve actuator-based droplet generator, for example.

Figure 1B:
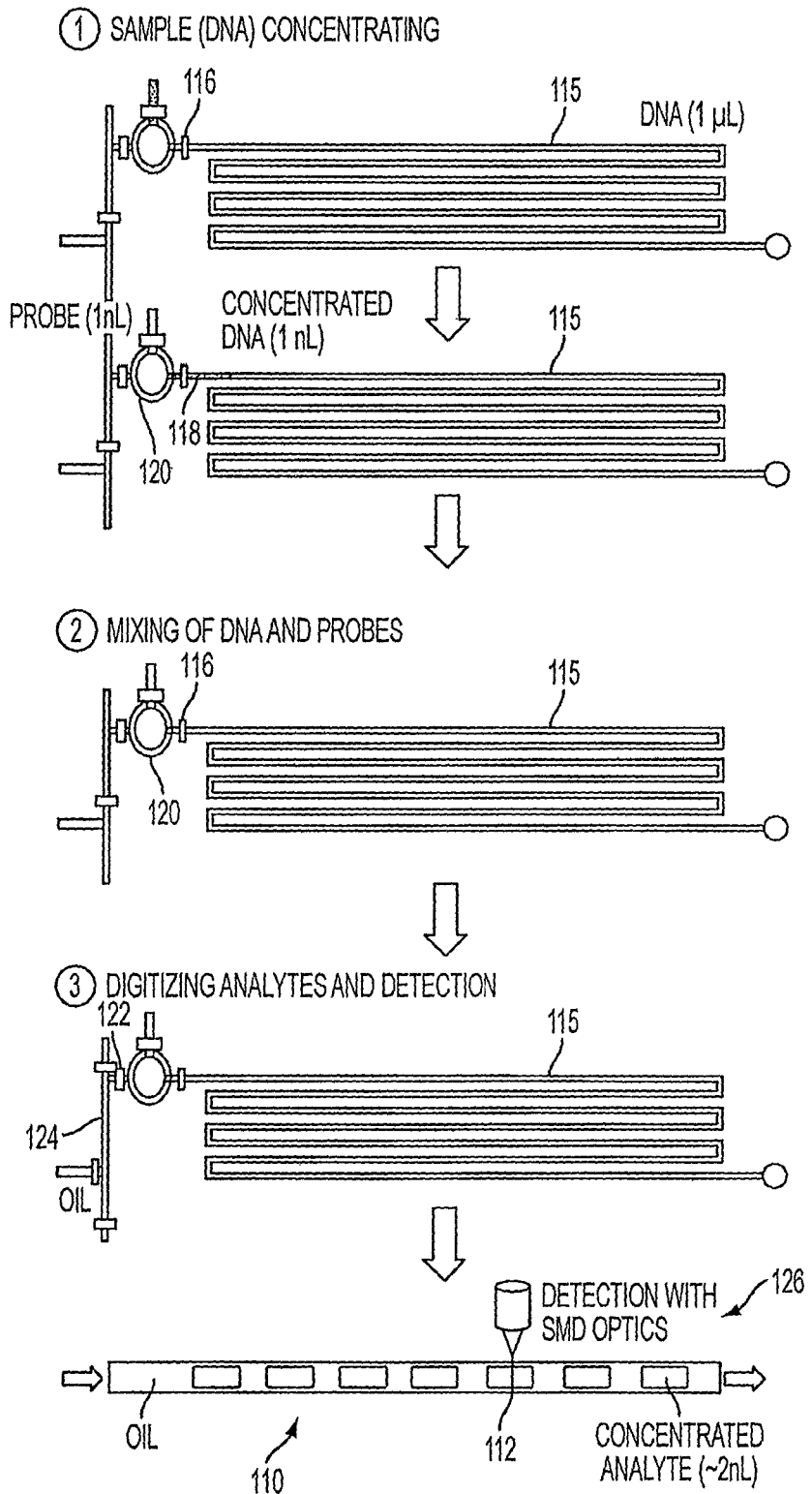
FIG. 1B is a schematic illustration to help facilitate the description of the operation of the microfluidic device of FIG. 1B.

FIG. 1B is a schematic illustration to facilitate the explanation of the operation of the microfluidic device 100. Fluid containing molecules and/or particles of interest is introduced into at least one concentration component 115 of the concentration section 106 through the input section 104. A portion of the solvent and/or other fluid in which the molecules and/or particles of interest are suspended is removed in the concentration component 115 while valve 116 is closed. For example, the fluid may contain DNA and/or other molecules of interest. The concentration component 115 can include a semi-permeable membrane in some embodiments of the current invention, which will be described in more detail below. In some embodiments of the current invention, input volumes of the order of micro liters can be reduced to volumes on the order of nano liters, thus resulting in a concentration of molecules and/or particles of interest by about three order of magnitude (about a factor of 1,000). However, the broad concepts of the current invention are not limited to specific levels of concentration.

Once the sample has been concentrated to provide plug 118, valve 116 is opened to allow the plug 118 to be forced into the mixing component 120 of mixing section 108. In this example, the mixing component 120 comprises a rotary chamber operable through peristaltic pumping by means of a plurality of valves around the rotary chamber. However, the mixing component is not limited to only rotary mixers. In other embodiments, serpentine mixers or other types of mixers could be used instead of or in addition to rotary mixers. Also, chaotic mixing structures within the channels could be included in some embodiments, such as structure to disrupt laminar flow to cause chaotic flow. The mixing component 120 can include one or more additional ports such that reagents and or other fluids can be directed into the rotary chamber to mix and/or react with molecules of interest in the plug 118. For example, fluorophores can be attached to molecules of interest, such as DNA molecules, at this stage. However, the broad concepts of the invention are not limited to this particular example. Other examples could include introducing various nanoparticles, quantum dots, etc. into the mixing component 120 according to the particular application.

After the mixing is complete, valve 122 is opened to direct plug 118 after mixing into the section 124 of the droplet generator 114. The droplet generator provides a fluid that is immiscible with the plug 118 in order to isolate the plug 118 from subsequent and/or preceding mixed plugs. For example, the molecules and/or particles of interest may be mixed and/or suspended in an aqueous solution to form a droplet in oil provided in the droplet generator. Alternatively, oil in water type droplets could be formed in some applications. A sequence of droplets are formed by sequential and/or parallel operation to the output channel 110 such that they pass through the detection region 112 of the output channel 110. The microfluidic device 100 can be used in conjunction with a detection system 126 to detect the molecules and/or particles of interest as they pass through the detection region 112. The detection system 112 can be an optical detection system in some embodiments of the current invention. In some embodiments, the detection system 126 can be a confocal spectroscopic system. In some embodiments, the detection system 126 can be a cylindrical illumination confocal spectroscopic system.

Figure 2A:
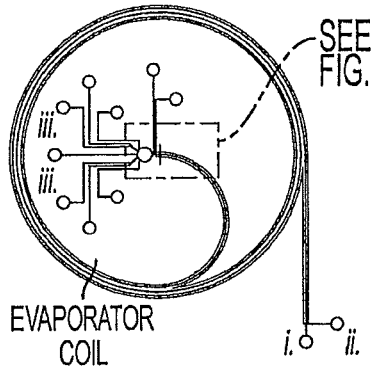
FIGS. 2A-2C are schematic illustrations of a microfluidic device according to another embodiment of the current invention.
Figure 2B:
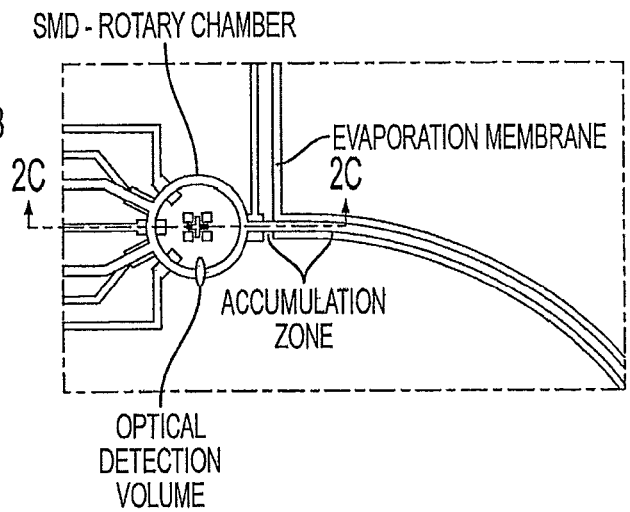
Figure 2C:
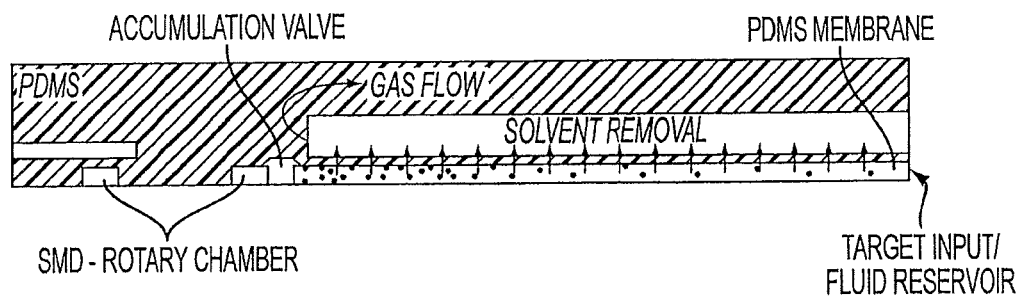

FIG. 2A is a schematic illustration of a microfluidic device according to another embodiment of the current invention. FIG. 2B shows an enlarged view of a section of FIG. 2A and FIG. 2C is a section taken as indicated in the section line of FIG. 2B. In this example, the concentration component of the concentration section is an evaporator coil. The section of FIG. 2C illustrates in more detail an embodiment of the concentration component. In this example, there is a semi-permeable membrane between the fluid channel and a gas flow channel that carries away solvent that passes through the semi-permeable membrane to the gas flow channel.

Figure 3A:
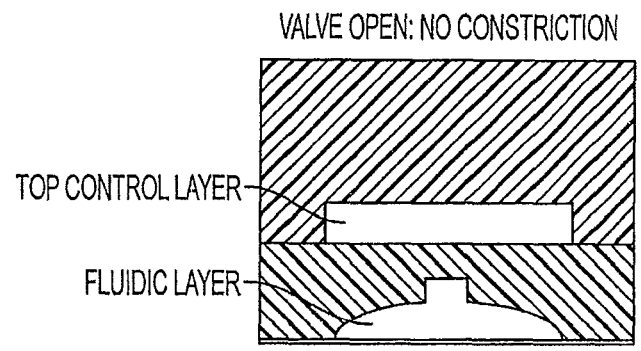
FIGS. 3A and 3B provide schematic illustrations of a detection channel for a microfluidic device according to another embodiment of the current invention.
Figure 3B:
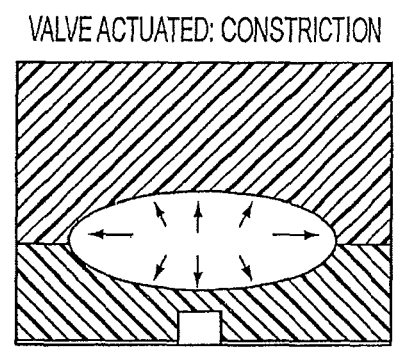

In some embodiments of the current invention, the detection region 112 has channel cross sectional area that can be changed from an initial area to a smaller area such that it acts to stretch out the droplet that is passing through it. FIGS. 3A and 3B provide an example of one embodiment of a detection channel that has a selectable, or changeable, cross sectional area. FIG. 3A is a cross section view of the detection region 112 in an open configuration. The open configuration can be substantially equal in cross sectional area as that of the output channel 110 immediately prior and subsequent to the detection region 112, for example. FIG. 3B shows a constricted configuration of the detection region 112. In this example, the detection region includes a detection channel and a deformable membrane such that the deformable membrane is operable to change the cross-sectional area of said detection channel.

An embodiment of the current invention provides a confocal spectroscopy system that can enable highly quantitative, continuous flow, single molecule analysis with high uniformity and high mass detection efficiency with a microfluidic device according to the current invention (See also U.S. application Ser. No. 12/612,300 assigned to the same assignee as the current application, the entire contents of which is hereby incorporated herein by reference in its entirety). Such a system will be referred to as a Cylindrical Illumination Confocal Spectroscopy (CICS) system. CICS is designed to be a highly sensitive and high throughput detection method that can be generically integrated into microfluidic systems without additional microfluidic components.

Rather than use a minute, diffraction limited point, CICS uses a sheet-like observation volume that can substantially entirely span the cross-section of a microchannel. It is created through the 1-D expansion of a standard diffraction-limited detection volume from approximately 0.5 fL to 3.5 fL using a cylindrical lens. Large observation volume expansions in 3-D (>100× increase in volume) have been previously performed to directly increase mass detection efficiency and to decrease detection variability by reducing the effects of molecular trajectory (Wabuyele, M. B., H. Farquar, W. Stryjewski, R. P. Hammer, S. A. Soper, Y. W. Cheng, and F. Barany. 2003. Approaching real-time molecular diagnostics: single-pair fluorescence resonance energy transfer (spFRET) detection for the analysis of low abundant point mutations in K-ras oncogenes. *J. Am. Chem. Soc.* 125:6937-6945; Habbersett, R. C., and J. H. Jett. 2004. An analytical system based on a compact flow cytometer for DNA fragment sizing and single-molecule detection. *Cytometry A* 60:125-134; Filippova, E. M., D. C. Monteleone, J. G. Trunk, B. M. Sutherland, S. R. Quake, and J. C. Sutherland. 2003. Quantifying double-strand breaks and clustered damages in DNA by single-molecule laser fluorescence sizing. *Biophys. J.* 84:1281-1290; Chou, H.-P., C. Spence, A. Scherer, and S. Quake. 1999. A microfabricated device for sizing and sorting DNA molecules. *Proceedings of the National Academy of Sciences* 96:11-13; Goodwin, P. M., M. E. Johnson, J. C. Martin, W. P. Ambrose, B. L. Marrone, J. H. Jett, and R. A. Keller. 1993. Rapid sizing of individual fluorescently stained DNA fragments by flow cytometry. *Nucl. Acids Res.* 21:803-806). However, these approaches often still require molecular focusing and/or unnecessarily compromise sensitivity since observation volume expansion in the direction of molecular travel is superfluous. For example, much pioneering work has been performed by Goodwin et al. in reducing detection variability through a combination of 3-D observation volume expansion (1 pL) and hydrodynamic focusing. While highly sensitive and uniform, these flow cytometry based methods use an orthogonal excitation scheme that is ill suited to incorporation with microfluidic systems. Chou et al., on the other hand, have performed a 3-D observation volume expansion to increase uniformity in an epi-fluorescent format for DNA sizing in a PDMS microfluidic device. The large size of the observation volume (375 fL) reduces signal-to-noise ratio and limits sensitivity to the detection of large DNA fragments (>1 kbp). Rather than a large 3-D expansion, a smaller 1-D expansion can be used to increase mass detection efficiency and increase detection uniformity while having a reduced effect on signal-to-noise ratio and detection sensitivity. 1-D beam shaping using cylindrical lenses has been recently applied in selective plane illumination microscopy (Huisken, J., J. Swoger, F. Del Bene, J. Wittbrodt, and E. H. K. Stelzer. 2004. Optical Sectioning Deep Inside Live Embryos by Selective Plane Illumination Microscopy. *Science* 305:1007-1009), confocal line scan imaging (Ralf, W., Z. Bernhard, and K. Michael. 2006. High-speed confocal fluorescence imaging with a novel line scanning microscope. *J. Biomed. Opt.* 11:064011), imaging-based detection of DNA (Van Orden, A., R. A. Keller, and W. P. Ambrose. 2000. High-throughput flow cytometric DNA fragment sizing. *Anal. Chem.* 72:37-41), and fluorescence detection of electrophoretically separated proteins (Huang, B., H. K. Wu, D. Bhaya, A. Grossman, S. Granier, B. K. Kobilka, and R. N. Zare. 2007. Counting low-copy number proteins in a single cell. *Science* 315:81-84) but have not been thoroughly explored in SMD. We present CICS as a confocal SMD system and method in which the trade-off between observation volume size, signal-to-noise ratio, detection uniformity, and mass detection efficiency can be easily modeled and optimized through 1-D beam shaping.

Figure 4A:
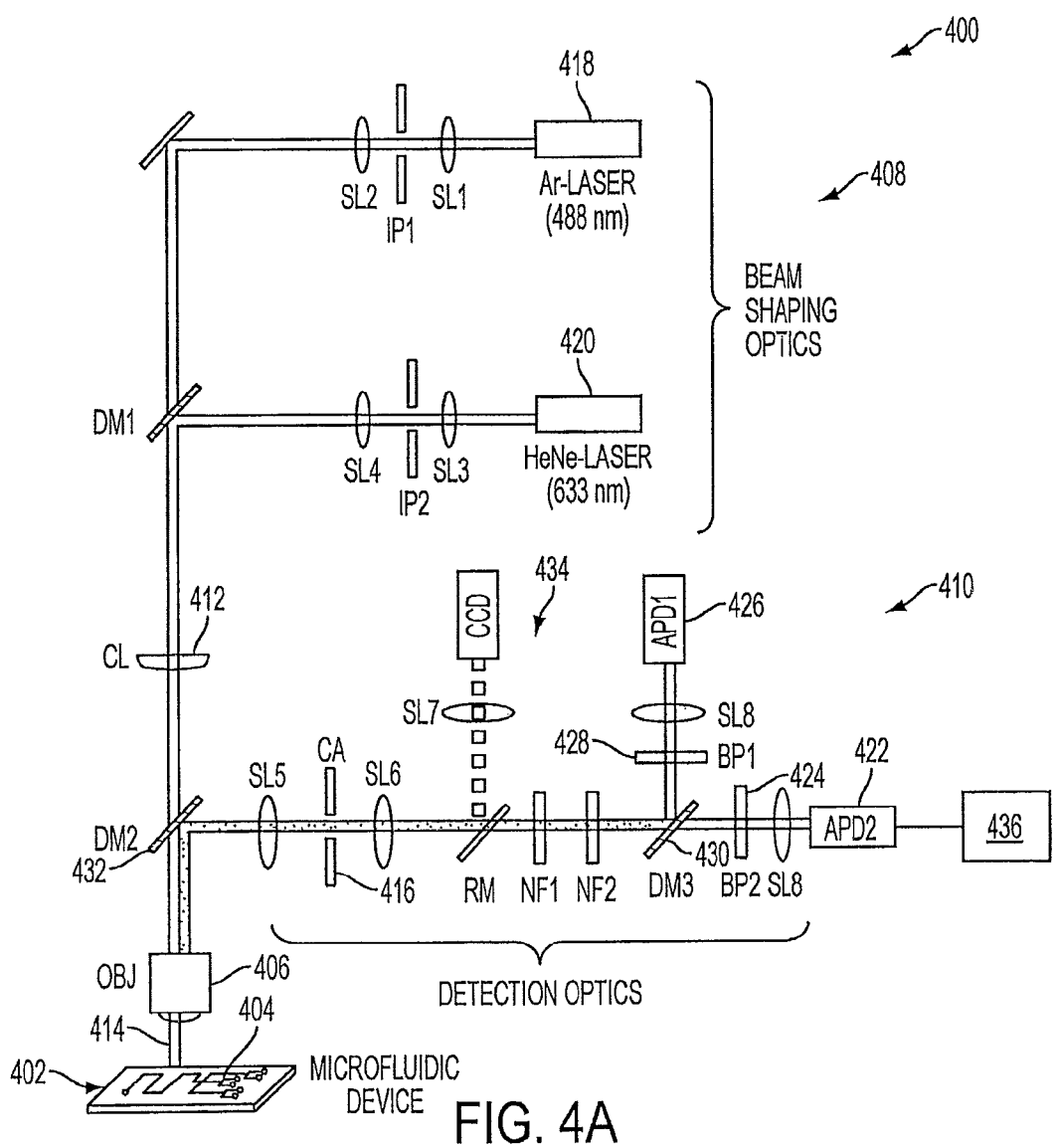
FIG. 4A is a schematic illustration of a cylindrical illumination confocal spectroscopy (CICS) system and a microfluidic device according to an embodiment of the current invention.
Figure 4B:
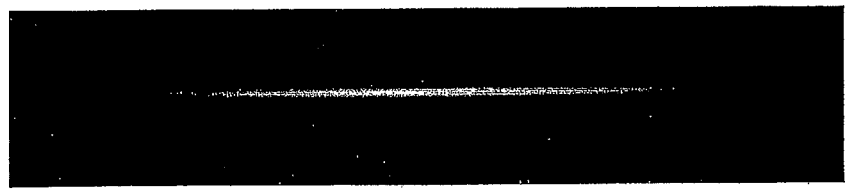
FIG. 4B shows reflected images of the illumination volume of the system of FIG. 1A, but with no aperture.
Figure 4C:
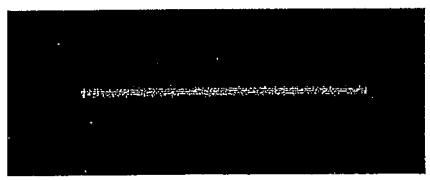
FIG. 4C corresponds to FIG. 4B, but a 620×115 µm rectangular aperture was included.
Figure 4D:
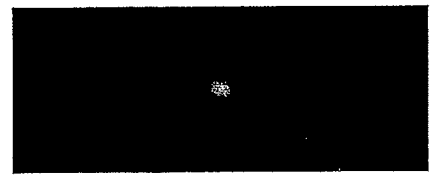
FIG. 4D is the case of conventional SMD with no pinhole. The conventional SMD illumination volume resembles a football that extends in and out of the plane of the page while the CICS observation volume resembles an elongated sheet or plane that also extends in and out of the page. The CICS observation volume is expanded in 1-D using a cylindrical lens (CL) and then filtered using a rectangular aperture (CA). In the absence of a confocal aperture in FIG. 4B, the CICS illumination profile is roughly Gaussian in shape along the x, y, and z axis, chosen to align with the width, length, and height of a microchannel, respectively. The addition of the confocal aperture in FIG. 4C, depicted as a rectangular outline, allows collection of fluorescence from only the uniform center section of the illumination volume. Abbreviations: SL—spherical lens, IP—illumination pinhole, CL—cylindrical lens, OBJ—objective, DM—dichroic mirror, CA—confocal aperture, BP—bandpass filter, RM—removable mirror, NF—notch filter, CCD—CCD camera, APD—avalanche photodiode.

FIG. 4A is a schematic illustration of a cylindrical illumination confocal spectroscopy system 400 according to an embodiment of the current invention. The cylindrical illumination confocal spectroscopy system 400 includes a fluidic device 402 having a fluid channel 404 defined therein, an objective lens unit 406 arranged proximate the fluidic device 402, an illumination system 408 in optical communication with the objective lens unit 406 to provide light to illuminate a sample through the objective lens unit 406, and a detection system 410 in optical communication with the objective lens unit 406 to receive at least a portion of light that passes through the objective lens unit 406 from the sample. The fluidic device 402 can be a microfluidic device such as described above with respect to FIGS. 1A-3B, for example. The illumination system 408 includes a beam-shaping lens unit 412 constructed and arranged to provide a substantially planar illumination beam 414 that subtends across, and is wider than, a lateral dimension of the fluid channel 404. The substantially planar illumination beam has an intensity profile that is wide in one direction orthogonal to the direction of travel of the beam (the width) while being narrow, relative to the wide direction, in another direction substantially orthogonal to both the direction of travel of the beam and the wide direction (the thickness). This substantially planar illumination beam is therefore a sheet-like illumination beam. The beam-shaping lens unit 412 can include, but is not limited to, a cylindrical lens. The detection system 410 includes an aperture stop 416 that defines a substantially rectangular aperture having a longitudinal dimension and a transverse dimension. The aperture stop 416 is arranged so that the rectangular aperture is confocal with an illuminated portion of the fluid channel such that the longitudinal dimension of the rectangular aperture substantially subtends the lateral dimension of the fluid channel without extending substantially beyond the fluid channel. In other words, the longitudinal, or long dimension, of the rectangular aperture is matched to, and aligned with, the illuminated width of the fluid channel 404. The transverse, or narrow dimension, of the rectangular aperture remains size matched to the narrow dimension, or thickness, of the illuminated sheet. Although the aperture is referred to as being substantially rectangular, it can be shapes other than precisely rectangular, such as an oval shape. In other words, the "substantially rectangular aperture" is longer in one dimension than in an orthogonal dimension. FIG. 4B shows the illumination light spread out to provide a substantially planar illumination beam 414. By arranging the substantially planar illumination beam 414 so that it extends sufficiently beyond the edges of the fluid channel 404 the bright central portion can be centered on the fluid channel. The aperture stop 416 can then be used to block light coming from regions outside of the desired illuminated slice of the fluid channel 404. The dimension of the beam expansion, the aperture size, and fluid channel size can be selected to achieve uniform detection across the channel according to an embodiment of the current invention. The beam is expanded such that the uniform center section of the Gaussian intensity profile covers the fluid channel. The remaining, non-uniform section is filtered out by the substantially rectangular aperture. For example, the substantially planar illumination beam incident upon said fluidic device is uniform in intensity across said fluid channel to within ±10% according to an embodiment of the current invention. To ensure that molecules within the microchannels are uniformly excited irrespective of position, the 1D beam expansion can be performed such that the max-min deviation across the microchannel is <20% according to some embodiments of the current invention. This leads to an optical measurement CV of ±6.5% due to illumination non-uniformity alone. For higher precision measurements, greater beam expansion can be performed at the cost of additional wasted illumination power. For example, given the same microchannel, a larger beam expansion can be performed such that the max-min variation is <5%, an optical measurement CV of <2% can be obtained.

In an embodiment of the current invention, we can use a 5 µm wide microchannel, for example. The aperture can be 600×50 µm (width×height). Given an 83-fold magnification, when the aperture is projected into sample space it ends up being about 7 µm wide, 2 µm wider than the channel. The laser beam is expanded to a $1/e^2$ diameter of about 35 µm, 7-fold wider than the channel width, where the excitation is most uniform. Thus, we only collect from the center 7 µm of the total 35 µm. Then, molecules flow through 5 µm of the available 7 µm (i.e., the microchannel). The narrow dimension of the aperture is size matched to the narrow, diffraction limited width the illumination line in the longitudinal direction to maximize signal to noise ratio. This provides approximately 100% mass detection efficiency with highly uniform beam intensity across the microchannel. However, the broad concepts of the current invention are not limited to this particular example.

The fluidic device 402 can be, but is not limited to, a microfluidic device in some embodiments. For example, the fluid channel 404 can have a width and/or depth than is less than a millimeter in some embodiments. The fluidic device can be, but is not limited to, a microfluidic chip in some embodiments. This can be useful for SMD using very small volumes of sample material, for example. However, other devices and structures that have a fluid channel that can be arranged proximate to the objective lens unit 106 are intended to be included within the definition of the fluidic device 402. For single fluorophore analysis, a fluid channel that has a width less than about 10 µm and a depth less than about 3 µm has been found to be suitable. For brighter molecule analysis, a fluid channel that has a width less than about 25 µm and a depth less than about 5 µm has been found to be suitable. For high uniformity analysis, a fluid channel has a width less than about 5 µm and a depth less than about 1 µm has been found to be suitable.

The objective lens unit 406 can be a single lens or a compound lens unit, for example. It can include refractive, diffractive and/or graded index lenses in some embodiments, for example.

The illumination system 408 can include a source of substantially monochromatic light 418 of a wavelength selected to interact in a detectable way with a sample when it flows through said substantially planar illumination beam in the fluid channel 404. For example, the source of substantially monochromatic light 418 can be a laser of a type selected according to the particular application. The wavelength of the laser may be selected to excite particular atoms and/or molecules to cause them to fluoresce. However, the invention is not limited to this particular example. The illumination system 408 is not limited to the single source of substantially monochromatic light 418. It can include two or more sources of light. For example, the illumination system 408 of the embodiment illustrated in FIG. 4A has a second source of substantially monochromatic light 420. This can be a second laser, for example. The second source of substantially monochromatic light 420 can provide illumination light at a second wavelength that is different from the wavelength from the first laser in some embodiments. Additional beam shaping, conditioning, redirecting and/or combining optical components can be included in the illumination system 408 in some embodiments of the current invention. FIG. 4A shows, schematically, an example of some additional optical components that can be included as part of the illumination system 408. However, the general concepts of the current invention are not limited to this example. For example, rather than free space combination of the illumination beam, the two or more beams of illumination light can be coupled into an optical fiber, such as a multimode optical fiber, according to an embodiment of the current invention.

The detection system 410 has a detector 422 adapted to detect light from said sample responsive to the substantially monochromatic light from the illumination system. For example, the detector 422 can include, but is not limited to, an avalanche photodiode. The detection system can also include optical filters, such as a band pass filter 424 that allows a selected band of light to pass through to the detector 422. The pass band of the band pass filter 424 can be centered on a wavelength corresponding to a fluorescent wavelength, for example, for the sample under observation. The detection system 410 is not limited to only one detector. It can include two or more detectors to simultaneously detect two or more different fluorescent wavelengths, for example. For example, detection system 410 has a second detector 426 with a corresponding second band pass filter 428. A dichroic mirror 430 splits off a portion of the light that includes the wavelength range to be detected by detector 426 while allowing light in the wavelength range to be detected by detector 422 to pass through. The detection system 410 can include various optical components to shape, condition and/or otherwise modify the light returned from the sample. FIG. 4A schematically illustrates some examples. However, the general concepts of the current invention are not limited to the particular example illustrated.

The cylindrical illumination confocal spectroscopy system 400 also has a dichroic mirror 432 that allows at least a portion of illumination light to pass through it while reflecting at least a portion of light to be detected.

The cylindrical illumination confocal spectroscopy system 400 can also include a monitoring system 434 according to some embodiments of the current invention. However, the monitoring system 434 is optional.

In addition, the detection system can also include a signal processing system 436 in communication with the detectors 422 and/or 426 or integrated as part of the detectors.

Some aspects of the current invention can include some or all of the following:

1) Microevaporators as Analytical Inputs from Large and Dilute Sample Volumes
   a. Solvent removal can be used to transport and confine low-abundant, target DNA molecules from large microliter volumes to nano-to-picoliter samples plugs. Microfluidic control of these low volume plugs can then used for highly efficient, post-evaporation, single molecule analysis.
   b. A range of solvents can be used in the pervaporator (i.e. ethanol or water), each can be chosen to match specific evaporation speeds or buffering capacity.
2) Inline, evaporators as inputs to Water-in-Oil Droplets
   a. Post-evaporation microfluidic control of the concentrated nano-to-picoliter sample plugs allows both introduction of fluorescent probes to the enriched target molecules and packaging of aqueous plugs into addressable water-in-oil droplets.
3) Tunable Molecular Detection Efficiencies from within Microfluidic Droplets using Fluorescence Confocal Spectroscopy
   a. Stretching the droplet reaction volumes through microfluidic confinements enables tunable molecular detection efficiencies, as each droplet passes through a laser illuminated optical probe volume with adjustable coverage of the droplet cross-sections. Traditional SMD or smaller detection volumes can be used for applications with less stringent requirements, while CICS can be used for 100% detection efficiencies.
4) Low Reagent Genomic Analysis
   a. The single molecule detection platform according to some embodiments of the current invention can provide parallel processing of nanoliter volumes containing picomolar concentrations of precious fluorescent probes, without the need for expensive amplification enzymes or molecule-surface conjugations. This is in contrast to conventional molecular amplification-based or microarray schemes for genomic analysis that require micromolar concentrations of probes for adequate reaction kinetics, or conventional single molecule detection platforms that must scan large sample volumes for individual molecules. Thus, use of this platform in a commercial setting for high-throughput genomic analysis can have a large potential for cost-savings through order-of-magnitude reagent reduction.
5) Low Run Time Single Molecule Assays
   a. The embodiments described herein can be designed according to the solvent removal capabilities of the microevaporators, as analysis of the contents of nano-to-picoliter droplets requires relatively little time. This efficiency does not exist in current single molecule detection platforms that require large preparation and run times to both bind specific biomolecules to molecular probe and scan those molecules from large sample volumes. Thus, use of this platform in a commercial setting can offer order-of-magnitude increases in throughput compared to conventional SMD schemes.
6) High-throughput, yet Low Volume Single Molecule Detection Assays
   The combination of the above features can offer the first platform for single molecule analysis that:
   a) directly interfaces a SMD platform with "macro-world" or pipette-able sample volumes,
   b) increases the number of these samples that can be analyzed within a given time without compromising single molecule sensitivity,
   c) takes advantage of amplification-free detection to truly decrease reagent consumption and assay times,
   d) and packages SMD into an automated, microfluidic platform, amenable to genomic applications.
7) Alternative Applications based on Traditional Amplification-based Detection The evaporator input to microfluidic droplets is not limited to SMD applications, but can also be used to augment technologies that it is otherwise meant to replace, such as, amplification-based detection schemes. For example, using the evaporator in PCR-based assays can result in:
   a) reduced number of amplification cycles or reduced assay times,
   b) decreased consumption of probe reagents, and
   c) increased throughput via sample enrichment.

EXAMPLES

In this example, we used inline, micro-evaporators according to an embodiment of the current invention to concentrate and transport DNA targets to a nanoliter single molecule fluorescence detection chamber for subsequent molecular beacon probe hybridization and analysis. This use of solvent removal as a unique means of target transport in a microanalytical platform led to a greater than 5,000-fold concentration enhancement and detection limits that pushed below the femtomolar barrier commonly reported using confocal fluorescence detection. This simple microliter-to-nanoliter interconnect for single molecule counting analysis resolved several common limitations, including the need for excessive fluorescent probe concentrations at low target levels and inefficiencies in direct handling of highly dilute biological samples. In this example, the hundreds of bacteria-specific DNA molecules contained in ~25 microliters of a 50 aM sample were shuttled to a four nanoliter detection chamber through micro-evaporation. Here, the previously undetectable targets were enhanced to the pM regime and underwent probe hybridization and highly-efficient fluorescent event analysis via microfluidic recirculation through the confocal detection volume. This use of microfluidics in a single molecule detection (SMD) platform delivered unmatched sensitivity and introduced complemental technologies that may serve to bring SMD to more widespread use in replacing conventional methodologies for detecting rare target biomolecules in both research and clinical labs.

INTRODUCTION

The development of microanalytical systems for biosensing is driven by advances in microfluidic control technologies for handling nano- to picoliter sample volumes (J. Melin and S. R. Quake, *Annu. Rev. Biophys. Biomol. Struct.*, 2007, 36, 213-231 (DOI:10.1146/annurev.biophys.36.040306.132646); S. Y. Teh, R. Lin, L. H. Hung and A. P. Lee, *Lab. Chip*, 2008, 8, 198-220 (DOI:10.1039/b715524g); S. Haeberle and R. Zengerle, *Lab. Chip*, 2007, 7, 1094-1110 (DOI:10.1039/b706364b)). However, the use of small sample volumes in these platforms also requires highly sensitive analyte detection schemes and it is the development and integration of these detection approaches, which remains one of the main challenges for the practical application of microfluidic devices (H. Craighead, *Nature*, 2006, 442, 387-393 (DOI:10.1038/nature05061); A. J. de Mello, *Lab. Chip*, 2003, 3, 29N-34N (DOI:10.1039/b304585b [doi])). Traditionally, laser-induced fluorescence (LIF) and methods for electrochemical detection provide the workhorse detection schemes for microanalysis, although recently there has been considerable progress in alternative detection techniques, such as, surface plasmon resonance (SPR), chemiluminescence, Raman, infrared, and absorbance-based detectors (A. J. de Mello, *Lab. Chip,* 2003, 3, 29N-34N (DOI:10.1039/b304585b [doi]); A. G. Crevillen, M. Hervas, M. A. Lopez, M. C. Gonzalez and A. Escarpa, Talanta, 2007, 74, 342-357 (DOI:10.1016/j.talanta.2007.10.019)). As the original detection technique LIF is most often used in conjunction with micro-capillary electrophoresis (CE) platforms, and this combination of separation and sensitive fluorescence detection remains one of the most represented classes of analytical Microsystems (A. G. Crevillen, M. Hervas, M. A. Lopez, M. C. Gonzalez and A. Escarpa, Talanta, 2007, 74, 342-357 (DOI:10.1016/j.talanta.2007.10.019)).

In parallel with these micro-CE platforms several researchers concentrate on the development of target-specific, amplification- and separation-free fluorescent biomolecular detection methods (A. Castro and J. G. Williams, *Anal. Chem.,* 1997, 69, 3915-3920; J. P. Knemeyer, N. Marme and M. Sauer, *Anal. Chem.,* 2000, 72, 3717-3724; H. Li, L. Ying, J. J. Green, S. Balasubramanian and D. Klenerman, *Anal. Chem.,* 2003, 75, 1664-1670; H. Li, D. Zhou, H. Browne, S. Balasubramanian and D. Klenerman, *Anal. Chem.,* 2004, 76, 4446-4451 (DOI:10.1021/ac049512c); C. Y. Zhang, H. C. Yeh, M. T. Kuroki and T. H. Wang, *Nat. Mater.,* 2005, 4, 826-831; C. Y. Zhang, S. Y. Chao and T. H. Wang, *Analyst,* 2005, 130, 483-488 (DOI:10.1039/b415758c); L. A. Neely, S. Patel, J. Garver, M. Gallo, M. Hackett, S. McLaughlin, M. Nadel, J. Harris, S. Gullans and J. Rooke, *Nat. Methods,* 2006, 3, 41-46 (DOI:10.1038/nmeth825); H. C. Yeh, Y. P. Ho, I. Shih and T. H. Wang, *Nucleic Acids Res.,* 2006, 34, e35 (DOI:34/5/e35 [pii]; 10.1093/nar/gkl021 [doi]); C. M. D'Antoni, M. Fuchs, J. L. Harris, H. P. Ko, R. E. Meyer, M. E. Nadel, J. D. Randall, J. E. Rooke and E. A. Nalefski, *Anal. Biochem.,* 2006, 352, 97-109 (DOI:10.1016/j.ab.2006.01.031); N. Marme and J. P. Knemeyer, *Anal. Bioanal Chem.,* 2007, 388, 1075-1085 (DOI:10.1007/s00216-007-1365-1); H. C. Yeh, C. M. Puleo, Y. P. Ho, V. J. Bailey, T. C. Lim, K. Liu and T. H. Wang, *Biophys. J.,* 2008, 95, 729-737 (DOI:10.1529/biophysj.107.127530)). In these methods, the confocal detection design of LIF enables ultrasenstitive, single-molecule detection (SMD), while several unique probe strategies, such as molecular beacons (T. H. Wang, Y. Peng, C. Zhang, P. K. Wong and C. M. Ho, *J. Am. Chem. Soc.,* 2005, 127, 5354-5359 (DOI:10.1021/ja042642i [doi]); H. C. Yeh, S. Y. Chao, Y. P. Ho and T. H. Wang, *Curr. Pharm. Biotechnol.,* 2005, 6, 453-461), two-color coincidence detection (H. C. Yeh, Y. P. Ho and T. H. Wang, *Nanomedicine,* 2005, 1, 115-121 (DOI:10.1016/j.nano.2005.03.004)), or additional FRET or PET-based probes facilitate specific molecular detection in a homogenous format. Although the sensitivity of LIF in detecting single fluorescent molecules yields infinitely low theoretical detection limits for biomolecular targets, the practical limitations of LIF-based SMD platforms are reported in the pM to fM range.

These common detection limits stem from two main challenges. The first is that analysis of probe-target interactions is complicated by free probe molecules. Although it is desirable to use high concentrations of probe molecules in order to increase probe-target interaction rates and ensure target saturation in a reasonable time, high excess probe causes increased background that prevents enumeration of single molecule fluorescence. For instance, although self-quenching probes, such as molecular beacons or smart probes, exhibit low background signals, the concentration of such probes still has to be restricted to the sub-nanomolar level in order to facilitate detection of single molecules. Previous attempts to deal with these complications include the use of fluorescent quenchers to suppress signal from unbound probe (R. L. Nolan, H. Cai, J. P. Nolan and P. M. Goodwin, *Anal. Chem.,* 2003, 75, 6236-6243) or the use of nanocrystals in unique FRET pairings, allowing for the use of increased probe concentrations to improve probe-target interactions. However, strategies such as these add cost and complexity to the assays and do not result in detection limits that breach the fM regime.

Secondly, nearly all of the successful applications of these SMD platforms utilize traditional means of analyte delivery, that is, fluorescently-labeled biomolecules are delivered to the focused laser observation volume through continuous flow within a microcapillary or microfabricated channel. In this case, the potential for assay miniaturization is confounded by inefficient fluidic couplings, reliance on external pumping systems, and size mismatch between the observation volume and flow cell. Indeed, these drawbacks restrict the use of homogenous, single molecule probe strategies, relegating them to isolated, large sample volume platforms with low mass detection efficiency. However, use of a closed-loop, rotary pump (H. P. Chou, M. A. Unger and S. Quake, *Biomed. Microdevices,* 2001, 3, 323-323-330) eliminates the extra fluid couplings associated with traditional SMD platforms and provides repeated, random sampling of probe-target interactions from nanoliter chambers (C. M. Puleo, H. C. Yeh, K. J. Liu and T. H. Wang, *Lab Chip,* 2008, 8, 822-822-825 (DOI:10.1039/b717941c)); thus, enabling new analyte delivery schemes tailored for discrete, low-volume SMD assays and specific biosensing strategies.

Herein, we describe a microfluidic coupling to deliver and concentrate targets to nanoliter-sized SMD chambers (C. M. Puleo, H. C. Yeh, K. J. Liu and T. H. Wang, *Lab Chip,* 2008, 8, 822-822-825 (DOI:10.1039/b717941c)) from otherwise undetectably low concentrations of sample DNA. In the design, a membrane-based, microfluidic evaporator serves as the input to a SMD rotary chamber and following solvent removal via evaporation, a concentrated sample plug is transferred for probe-target hybridization and interrogation via single molecule fluorescence burst counting. Though simple in design and function this unique means of analyte delivery represents a powerful method to overcome the traditional limitations associated with single molecule detection within microfluidic systems. First, the required fluorescent probe concentrations for efficient probe-target interactions within the highly dilute samples are minimized through target pre-concentration, thus diminishing the effect of background fluorescent events. In addition, direct measurements are made from clinically relevant microliter sample volumes through the use of micro-evaporators as unique interconnects between the dilute DNA samples and the nanoliter-sized SMD rotary chamber. Furthermore, application of this microfluidic detector-concentrator combination is shown to be ideal due to both the relatively gentle conditions necessary for solvent removal and the highly controlled rate of evaporation.

Indeed, desktop analyte concentration by solvent removal remains a mainstay in clinical and biological labs, as centrifugal and rotary evaporators are commonly used for nucleic acid preparation steps, during which DNA from large tissue samples are isolated into manageable sample sizes. This simple step has served as an enabling technique for the most highly sensitive, desktop biomolecular assays, such as polymerase chain reaction (PCR) and microarrays for decades.

Still, evaporation in microdevices is most often looked upon as a nuisance (Y. S. Heo, L. M. Cabrera, J. W. Song, N. Futai, Y. C. Tung, G. D. Smith and S. Takayama, *Anal. Chem.*, 2007, 79, 1126-1134 (DOI:10.1021/ac061990v); G. C. Randall and P. S. Doyle, *Proc. Natl. Acad. Sci. U.S.A.*, 2005, 102, 10813-10818 (DOI:10.1073/pnas.0503287102)) and utilization of solvent removal for practical applications remains rare (J. Leng, M. Joanicot and A. Adjari, *Langmuir*, 2007, 23, 2315-2315-2317; G. M. Walker and D. J. Beebe, *Lab. Chip*, 2002, 2, 57-61 (DOI:10.1039/b202473j [doi]); M. Zimmermann, S. Bentley, H. Schmid, P. Hunziker and E. Delamarche, *Lab. Chip*, 2005, 5, 1355-1359 (DOI:10.1039/b510044e)). Here, the practicality of coupling micro-evaporation with highly sensitive microanalytical platforms is demonstrated by decreasing the relative limit of detection of a common molecular beacon probe by over four orders of magnitude, thus surpassing previous limits set by more complex SMD probe schemes through a purely microfluidic means.

Materials and Methods

Microdevice Design

The devices, shown in FIG. 2A, were prepared as two layer PDMS (Sylgard 183) on glass using multilayer soft lithographic techniques (MSL) (M. A. Unger, H. P. Chou, T. Thorsen, A. Scherer and S. R. Quake, *Science*, 2000, 288, 113-116 (DOI:8400 [pii])), as described previously. FIG. 2B depicts the operation principles for pervaporation-based concentration (G. C. Randall and P. S. Doyle, *Proc. Natl. Acad. Sci. U.S.A.*, 2005, 102, 10813-10818 (DOI:10.1073/pnas.0503287102); J. Leng, B. Lonetti, P. Tabeling, M. Joanicot and A. Ajdari, *Phys. Rev. Lett.*, 2006, 96, 084503), as described in the results section. The cross-sectional dimensions of the fluidic channel measured 100 nm wide by 12 nm high, while the top, evaporation layer overlapped at slightly larger dimensions of 200 µm wide by 50 µm high. The PDMS membrane separating the two layers ranged from 20-30 µm with slight device-to-device variation. The sample inlet (labeled i.) of the fluidic channel was connected to a sample reservoir using 0.02" tygon tubing (Cole-Parmer) fitted with blunt-end, steel needle tips (McMaster-Carr, gauge 23). Access holes were punched in both layers using needle tips enabling device loading either directly from the tubing reservoir or gel-loading pipette tips for samples volumes as low as 0.1 µL.

Figure 5A:
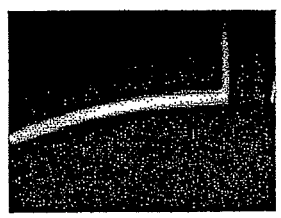
FIGS. 5A-5B show photo- and fluorescence micrographs of the accumulation zone just prior to the closed accumulation valve at time 0 after loading the evaporator coil with 500 nM fluorescently labeled DNA sequences in a microfluidic device according to an embodiment of the current invention.
Figure 5B:
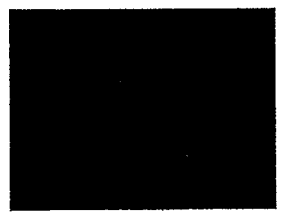
Figure 5C:
FIG. 5C is a fluorescence micrograph showing target accumulation after 6 hours of evaporation in the 1000 mm membrane pervaporator with 20 PSI nitrogen pressure and at room temperature.
Figure 5D:
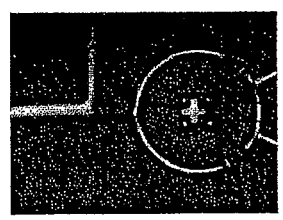
FIG. 5D is a photomicrograph of the SMD-rotary chamber just prior to sample injection with valves bisecting the chamber into analyte (left three-quarters) and probe/buffer (right one-quarter) compartments.
Figure 5E:
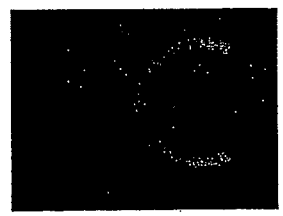
FIG. 5E is the accumulated model target from FIG. 5C injected into the rotary chamber along with DI water in the probe/buffer section.
Figure 5F:
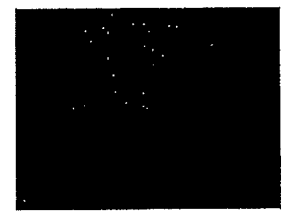
FIG. 5F shows mixing of the contents shown in FIG. 5E for 1 second using the rotary pump at 10 Hz, mixing was complete within 5 seconds (data not shown).

The SMD rotary chamber had dimensions of 1 mm loop diameter, 12 µm depth, and 100 µm width, while the intersecting valve control dimensions were 200 µm width by 50 µm depth. FIG. 5 depicts target accumulation at the inlet of this chamber during device operation and the loading steps for interrogation, with further description in the results section. The three valves trisecting the rotary chamber had two functions. First, they served to segment the chamber into multiple compartments to enable loading of multiple fluidic samples (FIGS. 5D and 5E). Second, actuation of the three valves in alternating patterns enabled peristaltic actuation of the four nanoliter sample within the chamber, creating a microfluidic rotary pump (FIG. 5F). All valve components of the device were primed with filtered water, controlled using the same needle tip connections used above, and pressurized with separate compressed air sources. Actuation sequences were programmed using an array of solenoid valves (Asco) and a Visual Basic (Microsoft) interface for an electrical switchboard (Agilent). Rotary actuation provided efficient mixing of the concentrated nanoliter plug with molecular probes and reaction buffers and enabled downstream recirculation for SMD analysis of specific biomolecules that accumulated during pervaporation (C. M. Puleo, H. C. Yeh, K. J. Liu and T. H. Wang, *Lab Chip*, 2008, 8, 822-822-825 (DOI: 10.1039/b717941c)).

The microdevices were coupled to a custom confocal fluorescence spectroscopic system by positioning the chip into a piezo-actuation stage capable of sub-micron resolution (Physik Instrumente) in order to focus the optical probe volume at the channel midpoint (C. M. Puleo, H. C. Yeh, K. J. Liu and T. H. Wang, *Lab Chip*, 2008, 8, 822-822-825 (DOI: 10.1039/b717941c)). A HeNe laser (633 nm, 25-LHP-151-249, Melles Griot) was expanded to match the back aperture of the focusing objective (100×, 1.4 N.A., UPlanFl, oil immersion, Olympus) after reflection by a dichroic mirror (51008 BS, Chroma Technology). During experiments the laser power was attenuated to ~100 µW by a neutral density filter before entering the objective and the beam was focused 6 µm into the channels, using the water-glass interface as a reference point. Emitted fluorescence was collected by the same objective, passed through a 50 µm pinhole (PNH-50, Melles Griot), and focused onto an avalanche photodiode (APD, SPCM-AQR-13, PerkinElmer) after band pass filtering (670DF40, Omega Optical). Acquisition software, written in Labview (National Instrument), and a digital counter (National Instrument) were used to collect data from the APDs. Threshold fluorescence values were determined by evaluating no target control samples, while single molecule events were defined by bursts within non-filtered data streams, where photon counts exceeded this preset threshold. Integration time for photon binning was set at 1 ms for all peak counting experiments, unless otherwise stated.

Pervaporation-Induced Flow Measurement

Previous groups described pervaporation induced flow, determining velocity distributions within the microchannel by assuming a constant volumetric flow rate of water through the PDMS membrane. In our study, bulk evaporation measurements were taken by evaluating the average displacement of the sample meniscus inside the reservoir tubing. In addition, time dependent fluctuations of the maximum pervaporation-induced flow rate was determined at the start of the membrane using an adaptation of a method previously described by our lab (S. Y. Chao, H. Yi-Ping, V. J. Bailey and T. H. Wang, *J. Fluoresc.*, 2007, 17, 767-767-774), in which the average duration of single molecule fluorescence bursts represent the flow-rate dependent transit time of molecules/particles passing through the optical detection volume. In these measurements, fluorescent bursts were measured using samples of $6\times10^8$ particles/mL, 0.1 µm tetraspec fluorescent beads (Molecular Probes) and the signal integration time for photon binning was set to 0.1 ms. Prior to burst analysis all flow measurement data was smoothed using the Lee Filter algorithm in order to provide more meaningful burst durations in low flow rate conditions (J. Enderlein, D. Robbins, W. Ambrose and R. Keller, *J. Phys. Chem. A*, 1998, 102, 6089-6089-6094; R. C. Habbersett and J. H. Jett, *Cyto. A*, 2004, 60A, 125-125-134). Stability of the evaporation induced flow was measured over time by monitoring fluorescent bursts in 100 s intervals, immediately following sample loading and commencement of gas flow within the top, evaporation channel. The effect of several operational parameters on flow rate control and stability were investigated, including evaporation chamber length, nitrogen flow rate, fluidic channel back-pressure, and device temperature.

Molecular Beacon (MB) Probe and Single Molecule Detection

A DNA-MB (5'-Cy5-CATCCGCTGCCTCCCGTAG-GAG TG-BHQ2-3' (SEQ ID NO: 1)) was synthesized by Integrated DNA Technologies (IDT) with the probe sequence (indicated in bold) complementary to a conserved region of the 16S rRNA in a wide-range of bacteria (C. Xi, L. Raskin and S. A. Boppart, *Biomed. Microdev.*, 2005, 7, 7-7-12). Complementary DNA oligonucleotides (IDT) were diluted in water and then loaded to fill a coiled, 1000 mm long channel. Pressurizing the reservoir tubing allowed complete dead-end filling, and maintained channel shape and sample continuity even at high nitrogen flow rates within the evaporation channel. For all experiments, both the back-pressure of the fluidic channel and the nitrogen pressure were kept equal (25 PSI for MB experiments), while control valves were actuated at 35 PSI to maintain closure. Control hybridization experiments were carried out without evaporation by loading the rotary pump with known concentrations of target DNA in water, then hybridizing the targets with MB probes (10 pM final concentration) loaded with hybridization buffer, in the second input. Prior to all hybridization experiments the microdevice was rinsed with a detergent (0.1% SDS) for ten minutes and filtered water for one hour, prior to drying in an oven overnight. The hybridization buffer was loaded with the probes to yield concentrations of 10 mM phosphate buffer (pH 7.8) and 900 mM NaCl after mixing and dilution with the target sample. The rotary pump was run at 100 Hz for 15 seconds upon loading of the rotary chamber with targets and probes, prior to heating the chip to 80° C. using a flat-bed thermocycler (custom Labnet MultiGene II) for 5 seconds and incubation at room temperature for one hour. After hybridization, the rotary pump was run at 100 Hz to recirculate sample through the optical probe volume and perform fluorescence burst counting for DNA detection within the four nanoliter chamber. Upon determining the detection limit under these condition, five incubation times were examined (5, 10, 15, 20, 30 minutes) to ensure optimal hybridization in subsequent concentrator experiments. The hybridization study was then repeated after accumulating DNA targets from samples at different concentrations using the evaporation channel, allowing determination of the efficacy of the combined evaporator-SMD microdevice. It is important to note that DNA targets were prepared from a 1 µM stock solution in 1×TE buffer by diluting to the experimental concentrations of 5-500 aM in purified water. Thus, these extreme dilutions rendered the effects of the original buffer concentration negligible, even after relatively large amounts of solvent removal.

Results and Discussion

Principle and Operation of the Microfluidic Device

As shown in FIGS. 2A-2C, solvent in the bottom, fluidic layer pervaporated through the thin PDMS membrane separating this sample layer and the evaporation channel. Evaporated solvent was replaced through convection from a sample reservoir (labeled i.), while dry nitrogen was flown through the evaporation channel (labeled ii.) to maintain a more constant driving force for pervaporation throughout the device. In this example, accumulation of analyte was accomplished through the incorporation of a MSL valve (accumulation valve) to interrupt the convective flux from the reservoir. The fluidic and evaporation channels were coiled from this dead-end valve, allowing fabrication of devices with pervaporation membranes from 5 mm to 2000 mm in length. The reversible, MSL valve allowed manipulation of the concentrated sample plugs, which form after solvent removal and solute accumulation. FIG. 5 shows the accumulation of model, FAM-labeled, single stranded DNA (500 nM, 23 nt sequence, IDT) at this dead-end valve (FIG. 5C), followed by subsequent release of the valve and transfer of the concentrated nanoliter-sized sample plug to a downstream SMD rotary chamber (FIG. 5E). Images of the model fluorescent targets were taken using a 5× objective (Olympus BX51) and a cooled CCD camera (RetigaExi, QImaging Corporation) at 2 second exposure time. In MB experiments, probes and hybridization buffer were then loaded into the remaining portion of the rotary chamber for subsequent mixing with the concentrated sample plug (FIG. 5F) and recirculating SMD.

Device Characterization

Figure 6A:
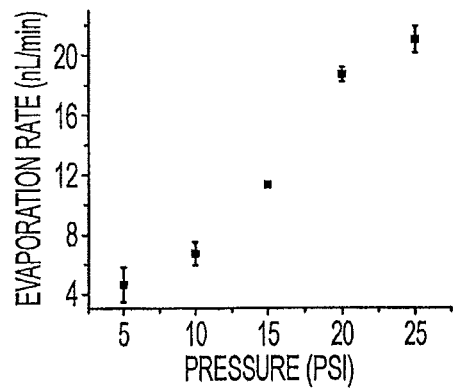
FIGS. 6A-6C show bulk evaporation rates versus evaporation pressure (FIG. 6A), microdevice temperature (FIG. 6B), and evaporation membrane length (FIG. 6C) according to an embodiment of the current invention. Pressure data was taken using a 1000 mm membrane at room temperature. Temperature data was taken using a 1000 mm membrane at 25 PSI, while evaporation length data was taken at room temperature and 25 PSI.
Figure 6B:
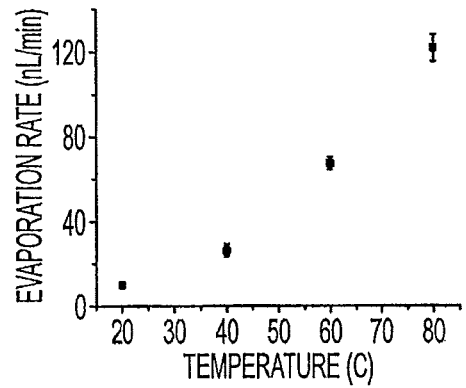
Figure 6C:
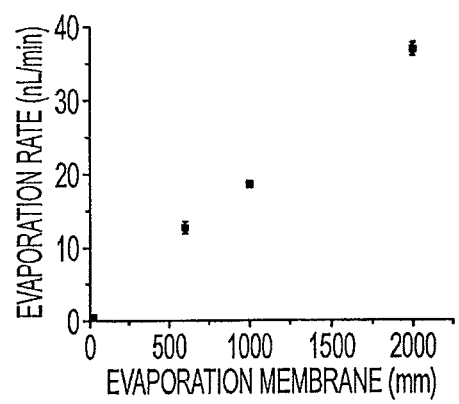

As discussed previously, the compensating flow from the fluid reservoir must equal the volumetric flow rate achieved by the pervaporation membrane. Therefore, the effectiveness of coupling the concentrator to the SMD rotary chamber is dependent on the magnitude and stability of the volumetric flow rate due to evaporation, which were measured both by quantifying average burst durations of polymer beads just upstream of the channel entrance and by observing the motion of the meniscus within the tubing reservoir. FIG. 6 shows average evaporation rates within the microdevice after altering various operational parameters, including applied pressure, temperature, and evaporation membrane length. The increasing evaporation rates with nitrogen pressure (FIG. 6A) were likely attributable to the faster nitrogen flows within the device, which act to purge water vapor and minimize diffusive boundary layers across the pervaporation membrane. In all experiments, back-pressure applied to both the sample channel and nitrogen flow channels were increased simultaneously and increasing sample pressure alone had little effect on the non-negligible evaporation rates with zero applied nitrogen flow (data not shown). However, this effect of nitrogen flow on evaporation rate is limited, as higher flow rates eventually result in constant driving forces for evaporation within the device, and interfaces between device layers often fail at back-pressures approaching 40-50 PSI. Still, several additional methods exist for increasing evaporation rates and thus the efficacy of the combined concentrator-detector. FIG. 6B shows the evaporation rates from a 1000 mm pervaporator when held at various temperatures using a flatbed thermocycler, with a maximum rate of ~120 nL/min at 80° C., while FIG. 6C shows rates from microdevices held at room temperature (~25° C.) with varying evaporation membrane lengths. Importantly, while not fully optimized in this example, the dependence of evaporation rates on multiple device parameters enables concentration approaching the hundreds of microliters per hour rates associated with desktop evaporators (Genevac, Ltd., EZ-Bio, "Second Generation Evaporation/Concentration System for Life Science Laboratories," www.genevac.com, 2008). In addition, elimination of any air-liquid interface in the membrane-based microfluidic evaporator eradicates spurious convective flows or bumping, which may cause sample-loss or cross contamination in alternative macro- or micro-evaporator designs (C. M. Puleo, H. C. Yeh, K. J. Liu, T. Rane and T. H. Wang, *Micro Electro Mechanical Systems*, 2008. MEMS 2008. *IEEE 21st International Conference on,* 2008, 200-203). Furthermore, the low thermal mass within the micro-evaporator permits isothermal conditions gentle enough to preserve the activity of biological species, while integration of the evaporator with MSL control technologies allows direct coupling of the analytical component of the microdevice, thereby maximizing sensitivity.

Figure 6D:
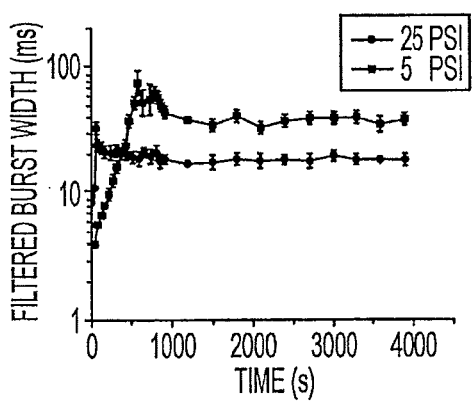
FIG. 6D shows time trace of the measured fluorescent burst duration of tetraspec beads at the start of the evaporation channel at two different evaporation pressures (25 and 5 PSI). Large fluctuations at low pressure are due to evaporation membrane vibration upon initiation of nitrogen flow. Points for A, B, and C are mean evaporation rates from a single device after three separate two hour measurements±standard error.

FIG. 6D shows a time trace of the average fluorescent burst duration of fluorescent beads within a 1000 mm, coiled pervaporation chamber immediately following the start of nitrogen circulation within the top channel. Unlike the bulk evaporation data presented thus far, the single particle measurements show large transient sample flows and non-negligible latency times (up to 15 minutes) due to vibrations of the coiled membrane at low applied nitrogen pressures. The large sample flow rates (short burst durations) observed immediately after commencement of nitrogen flow is followed by sample flow cessation (long burst durations), which is caused by reflection of the vibration induced sample convection at the dead-end or accumulation valve. After damping of this transient flow, burst durations reach a stable value, which persist throughout device operation. Increasing the back-pressure applied to the fluid and gas channels (25 PSI) lead to faster damping of this transient flow and steady evaporation within seconds, thus allowing device operation with minimal latency times.

Attomolar Detection of DNA Targets with Molecular Beacons

Figure 7:
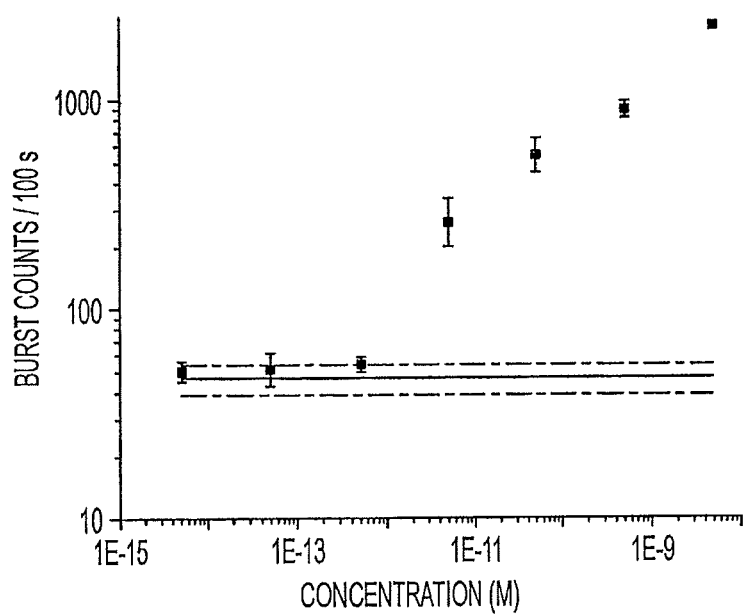
FIG. 7 shows calibration curve of fluorescence burst counts versus target concentration loaded into the SMD-rotary chamber without evaporation-based accumulation (10 pM molecular beacon concentration). The solid line represents the average number of fluorescent bursts from the no target control (dotted line equals one standard deviation from an average of four measurements).
Figure 8:
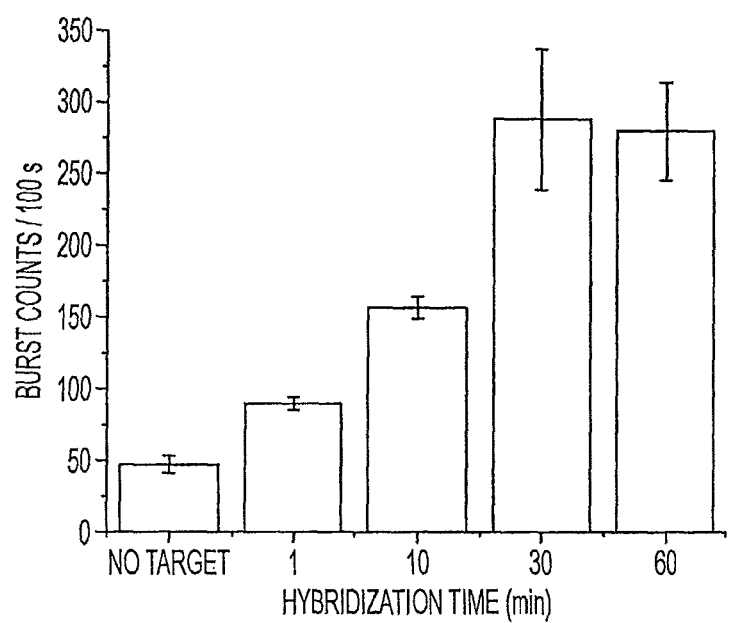
FIG. 8 shows number of fluorescent bursts detected versus hybridization time (5 pM targets, 10 pM probe) within the device according to an embodiment of the current invention. Hybridization time follows a 15 second mixing period using the rotary pump and a 5 second incubation at 80° C.

FIG. 7 shows the fluorescence burst data for control MB hybridization experiments within the microdevice, without the use of the evaporator. In bulk studies, dual-labeled, hairpin probes commonly increase in fluorescence intensity from 10-100 fold upon hybridization to complementary targets (A. Tsourkas, M. A. Behlke, S. D. Rose and G. Bao, *Nucleic Acids Res*, 31, 1319-1319-1330). This signal-to-background ratio is limited by the need to design hairpins with stem structures long enough to minimize signal from non-bound probes, yet short enough to provide instability to allow probe-target hybridization within reasonable timescales. These design criteria have restricted the use of molecular beacons in homogenous, single molecule assays, where signal from thermally fluctuating MBs become indistinguishable from bound probes at low target concentrations, as shown in FIGS. 7 and 8. Limitations such as these have led researchers to develop alternative FRET-based and coincident probe schemes specifically designed to increase signal-to-background ratios in single molecule studies.

Still, probe-target reactions in these traditional SMD studies are typically conducted for hours prior to running confocal fluorescence detection experiments and the overall sensitivity is still limited to fM. These limits are due in part to the restricted molecular probe concentrations (nM-pM) required to maintain low levels of background fluorescence for SMD measurements, discussed previously. In addition, the long probe-target incubation times for SMD, extended read times reported to gain reliable results, and difficulties in handling rare target molecules remain persistent barriers against more widespread use for quantification of biomolecules. FIG. 8 shows the hybridization time required to obtain a maximum fluorescence burst count after loading 5 pM DNA targets into the microdevice. After mixing and hybridization, the MB signal saturates within a <30 min incubation time, significantly reducing the reaction time required for experiments in which target concentrations have been enhanced to this level, compared to direct quantification from dilute or sub-picomolar concentrations using traditional SMD platforms. Thus, the rate limiting step in fluorescent event counting assays within the evaporator-SMD microdevice becomes solvent removal, which is a controllable device parameter (FIG. 6).

The unique micro-evaporator coupling to single molecule assays allows direct analysis from microliter-sized, low abundant, purified DNA solutions eliminating additional sample handling, in which variability could be introduced when using traditional SMD platforms. Importantly, solvent removal remains a viable option for nucleic acid concentration since several nucleic acid isolation protocols allow for washing or desalting of DNA, including phenol extraction/ethanol precipitation or elution using glass beads (D. Moore, "Purification and concentration of DNA from aqueous solutions." Curr Protoc Immunol. 2001, pp. 10.1). Resuspension in purified water does not alter DNA integrity, while stringent cleaning protocols for the microdevice enables removal of large amounts of solvent for concentration factors reaching 1,000's with little effect on subsequent hybridization reactions. In addition, probe introduction to the microdevice takes place following solvent removal from separate device inlets facilitating hybridization reactions within buffered and controlled conditions that are independent of the concentration step. This becomes especially important when using hairpin probes, such as molecular beacons, since several important probe properties, including signal-to-background ratio and specificity, are altered dramatically in solutions with differing ionic strengths (Z. Tang, K. Wang, W. Tan, J. Li, L. Liu, Q. Guo, X. Meng, C. Ma and S. Huang, *Nucleic Acids Res.*, 2003, 31, e148). Indeed, these requirements highlight the advantage of performing recirculating SMD within a microdevice amenable to arrayed formats for probing optimal buffer conditions from concentrated sample plugs.

Figure 9A:
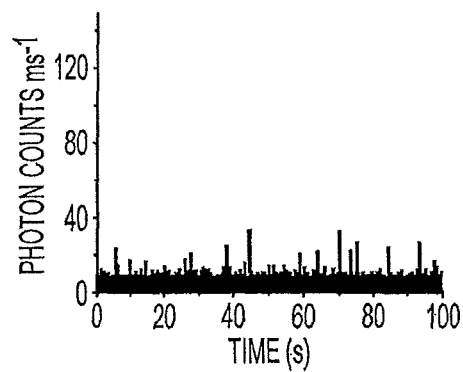
FIGS. 9A-9B show raw fluorescence burst traces from the recirculating SMD chamber (100 Hz pump frequency) after 20 hours of target enrichment and probe hybridization with no target control (A) and 50 aM target (B) samples according to an embodiment of the current invention.
Figure 9B:
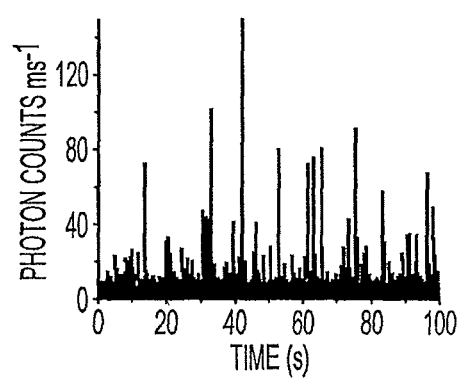
Figure 9C:
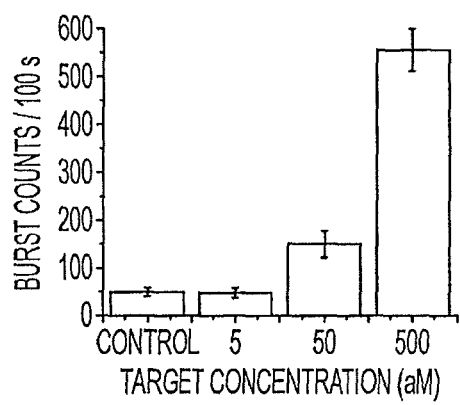
FIG. 9C shows number of fluorescent bursts detected versus loading concentration after 20 hours of evaporation within the 1000 mm membrane device (10 pM probe, room temperature, 25 PSI), along with no target controls.

As shown in FIG. 5, target DNA is advected toward the dead-end valve during evaporation where it accumulates for subsequent transfer and detection within the SMD rotary chamber. The width of this accumulation zone is dependent on backwards thermal diffusion of the concentrated species. As shown in FIG. 5C, the width of target accumulation is comparable to the volume swept into the rotary pump for SMD; therefore, the rate of concentration within the microdevice is directly dependent on increase in target concentration within this accumulation zone. At large running times the growth of this accumulation zone can be estimated using the time scale associated with emptying one complete evaporator channel volume or $t_e = h/v_e$, where h is the height the channel and $v_e$ is the evaporation velocity through the pervaporation membrane. Evaporation velocity is calculated over the total pervaporation surface (S) as $v_e = Q_e/S$, where $Q_e$ is the measured volumetric flow rate achieved through solvent removal. Evaporation at 25 PSI nitrogen pressure results in an estimated $Q_e$ of 21.63 nL/min, as shown above, giving a $t_e$ value of ~55 minutes and a target flux of $J = Cv_e$ within that time, where C represents the concentration of target within the sample reservoir. At this rate of evaporation the longest concentration time attempted in this report resulted in removal of ~26 μL of solvent or a ~6500-fold enhancement in target concentration within the 4 nanoliter SMD chamber. In the molecular beacon calibration curve (FIG. 7), the pM level burst count response above background reveals that the above level of target enhancement would yield theoretical detection limits approaching 200 aM after solvent removal. Indeed, FIG. 9 validates this aM level detection limit after evaporation, showing a measured limit of 50 aM after evaporation. The 4-fold discrepancy between the measured and expected detection limits may be attributable to chip-to-chip variations in evaporation rates due to membrane thickness or alignment. In addition, while the evaporation coil may serve as an interconnect to large clinical sample volumes, the dilute DNA solutions used in this report must be prepared through serial dilutions and are subject to pipetting errors. Still, as shown the enrichment of the 100 s of target molecules (FIG. 9B) from the aM sample was sufficient for detection above the background fluorescent bursts (FIG. 9A) resulting from thermal fluctuations of the 1000 s of MB probes injected into the SMD chamber. These results demonstrate efficient transport of the low abundant DNA molecules through the relatively inert PDMS evaporator. Furthermore, it is noteworthy that enumeration of these few hundred molecules ferried to the 4 nanoliter SMD chamber would still pose quite a challenge were it not for the application of recirculating confocoal fluorescence detection. Resampling within the discrete nanoliter chamber enables utilization of the majority of the molecular information contained in the SMD chamber in relatively short read times, thus permitting the unique combination of an evaporation-based concentrator and SMD. In addition, FIG. 6 shows that modification of simple operating parameters explored in this example lead to $Q_e$ values of 100's nanoliters per minute, showing that the evaporation time necessary for achieving these detection limits can be drastically reduced. Even so, to our knowledge this represents the first practical report of attomolar sensitivity using single molecule fluorescence counting or common hairpin probes.

CONCLUSIONS

Novel means of analyte delivery are necessary in order to breach the common femtomolar detection limits in current microfluidic platforms (P. R. Nair and M. A. Alam, *Appl. Phys. Lett.*, 2006, 88, 233120; P. E. Sheehan and L. J. Whitman, *Nano Lett.*, 2005, 5, 803-807 (DOI:10.1021/n1050298x [doi])). Microevaporators represent a unique method to bridge the gap between real-world, microliter biological samples and the nano- to picoliter detection volumes within microanalytical systems. Specifically, the well-controlled evaporation rates within microdevices enable highly reproducible transfer of a small number of molecular targets to specified detection components within microfluidic networks. In this example, DNA targets are detected at initial concentrations as low as 50 aM using a simple hairpin probe. Thus, the novel scheme of using solvent removal for analyte transfer to a nanoliter-sized detection volume not only obviates the need for special fluorescent probes designed specifically for confocal fluorescence detection, but surpasses the detection limits of these probes used in normal microfluidic platforms. Key to this result is performing single molecule fluorescence detection within a closed-loop rotary pump, which decreases the hybridization assay volume by orders of magnitude, thus allowing direct coupling to the microfluidic evaporator. In addition, detection is made from the typical starting volumes normally handled with pipettes and benchtop processing techniques, rendering the microdevice compatible with common nucleic acid isolation procedures, such as alcohol precipitation and affinity-based separation, which result in resuspension of small amounts of DNA in microliters of water.

Microevaporators could easily be integrated with other detection schemes, such as disk and wire-like nano-biosensors (Z. Gao, A. Agarwal, A. D. Trigg, N. Singh, C. Fang, C. H. Tung, Y. Fan, K. D. Buddharaju and J. Kong, *Anal. Chem.*, 2007, 79, 3291-3291-3297; F. Patolsky, G. Zheng and C. M. Lieber, *Nanomed.*, 2006, 1, 51-51-65) to increase analyte transfer and kinetics of target capture. Detection chambers for these nanoscale biosensors could reach picoliter levels, enabling concentration factors surpassing the ~6500 shown using nanoliter chambers in this example. Indeed, optimization and standardization of microevaporators as universal analyte inputs to microanalytical systems could lift many of the current limitations of conventional microfluidic delivery systems. Additional improvements to membrane-based evaporators could include ion permeable membranes, enabling control over buffer concentrations during solvent removal, thus expanding applicability to complex protein and microorganism containing samples. Further modifications to the evaporator coil could also include the use of three-dimensional microstructures to maximize the surface area of the pervaporation membrane, which would lead to increases in assay sensitivity, while substantially decreasing total processing time. In this manner, processing times for single molecule detection platforms, such as single molecule fluorescence counting, that are traditionally limited due to probe-target hybridization kinetics would become dominated by the controllable evaporation or enrichment speeds within the evaporation-based analyte input. In addition, utilizing solvent removal as a simple method of analyte transport alleviates many of the challenges involved with low-volume sample processing and the lack of compatibility between conventional lab methodologies and SMD. Therefore, these results represent a clear example that for specific biological applications the performance of any microanalytical device must be assessed by the sensitivity of the sum of its parts, and not just the responsivity of its probe.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A method of detecting particles, comprising:

inputting a sample comprising particles to be detected into an input channel of a microfluidic device of a microfluidic detection system, said sample further comprising a first fluid in which said particles are at least one of suspended or dissolved;

concentrating said sample in a sample concentration section of said microfluidic device by removing at least a portion of said first fluid through a solvent-permeable membrane of said microfluidic device to provide a concentrated sample;

mixing said concentrated sample in a mixing section of said microfluidic device with a reagent to label said particles to be detected using said microfluidic device to provide a concentrated, labeled sample;

generating a droplet from said concentrated, labeled sample in an output channel of said microfluidic device using a droplet generator of said microfluidic device such that said droplet is isolated by a second fluid that is immiscible with said first fluid;

repeating said inputting, said concentrating, said mixing and said generating a plurality of times to provide a plurality of droplets in said output channel; and detecting, sequentially, said particles in each of said plurality of droplets after said mixing based on a response of said labels, wherein said solvent-permeable membrane is at least partially permeable to a solvent in which said sample will be mixed during operation, wherein said sample is greater than about 1 microliter and less than about 1 milliliter, and wherein said concentrated sample is reduced in volume by a factor of at least 100.

2. The method of detecting particles according to claim 1, wherein said concentrated sample is less than 100 nanoliters.

3. The method of detecting particles according to claim 1, wherein said particles are single molecules.

4. The method of detecting particles according to claim 1, wherein said mixing said concentrated sample with said reagent labels said particles to be detected with fluorescent molecules, and wherein said detecting comprises illuminating said particles to be detected to cause said fluorescent molecules to emit fluorescent light to be detected.

5. The method of detecting particles according to claim 4, wherein said illuminating comprises illuminating said sample with a substantially planar beam of light to perform cylindrical illumination confocal spectroscopy.

6. The method of detecting particles according to claim 1, wherein said repeating is performed at least partially in parallel so that more than one droplet is produced substantially simultaneously.

7. The method of detecting particles according to claim 1, wherein said repeating is performed for a period of time such that said detecting is substantially a continuous-flow detection for a period of time.

8. The method of detecting particles according to claim 1, wherein said generating said droplet comprises hydrodynamic focusing.

9. The method of detecting particles according to claim 1, wherein said mixing comprises at least one of peristaltic pumping or chaotic mixing.

* * * * *